United States Patent [19]

Trouet et al.

[11] Patent Number: 4,639,456
[45] Date of Patent: * Jan. 27, 1987

[54] VINBLASTIN-23-OYL AMINO ACID DERIVATIVES

[75] Inventors: Andre B. L. Trouet, Winksele; Jean A. A. J. Hannart, Dion Valmont; Kandukuri S. B. Rao, Rosieres, all of Belgium

[73] Assignee: Omnichem S.A., Belgium

[*] Notice: The portion of the term of this patent subsequent to Jun. 14, 2000 has been disclaimed.

[21] Appl. No.: 446,708

[22] Filed: Dec. 3, 1982

Related U.S. Application Data

[63] Continuation-in-part of Ser. No. 269,876, Jun. 3, 1981, Pat. No. 4,388,305.

[30] Foreign Application Priority Data

Jun. 10, 1980 [LU]  Luxembourg ............... 82514
Dec. 23, 1980 [LU]  Luxembourg ............... 83034
Dec. 8, 1981 [LU]   Luxembourg ............... 83822

[51] Int. Cl.$^4$ ............. C07D 519/04; C07D 47/16; A61K 31/40
[52] U.S. Cl. ................... 514/283; 514/17; 514/18; 514/19; 540/478
[58] Field of Search ............ 260/244.4, 112.5 R; 424/262, 177; 514/283

[56] References Cited

U.S. PATENT DOCUMENTS

| | | | |
|---|---|---|---|
| 4,029,663 | 6/1977 | Gutowski et al. | 260/244.4 |
| 4,144,237 | 3/1979 | Kutney | 260/244.4 |
| 4,203,898 | 5/1980 | Cullinan et al. | 260/244.4 |
| 4,388,305 | 6/1983 | Trouet et al. | 424/177 |
| 4,430,269 | 2/1984 | Pearce | 260/244.4 |

FOREIGN PATENT DOCUMENTS

| | | | |
|---|---|---|---|
| 2078730 | 1/1982 | United Kingdom | 260/244.4 |
| 2090837 | 1/1982 | United Kingdom | 424/262 |

OTHER PUBLICATIONS

Lewin et al., Heterocycles, vol. 14, No. 12, pp. 1915-1920 (1980).

Primary Examiner—Donald G. Daus
Assistant Examiner—William A. Teoli, Jr.
Attorney, Agent, or Firm—Ostrolenk, Faber, Gerb & Soffen

[57] ABSTRACT

Vinblastine derivatives of the formula (I)

wherein $R_1$ is an ester of a α-aminoacid selected from the group consisting of glycine, alanine, valine, leucine, isoleucine, serine, threonine, aspartic acid, glutamic acid, aspargine, glutamine, arginine, lysine, cysteine, cystine, methionine, phenylalanine, tyrosine, tryptophan, proline, histidine, hydroxy-lysine, hydroxyproline, or of a peptide consisting of 1-6 identical or different such amino-acids, and the ester group, which may be straight or branched, being a carboalkoxy group having 2-9 carbon atoms, and $R_2$ is hydrogen or a $C_2$-$C_9$ alkanoyl group, $R_5$ is H or OH, $R_6$ is $CH_3$, CHO or H and X=H or Br and their pharmaceutically acceptable mineral or organic acid addition salts. The compounds are useful as antitumor drugs.

20 Claims, No Drawings

VINBLASTIN-23-OYL AMINO ACID DERIVATIVES

This is a continuation-in-part of application Ser. No. 269,876, filed June 3, 1981 and now U.S. Pat. No. 4,388,305.

FIELD OF THE INVENTION

This invention relates to novel bisindole alkaloids. More particularly, the invention relates to amino acid derivatives of vinblastine or vinblastine-related alkaloids, including peptide derivatives, to methods for their preparation, and to pharmaceutical compositions containing such vinblastine derivatives as antitumor agents, and particularly for use in treating malignant tumors in humans.

REPORTED DEVELOPMENTS

Bisindole alkaloids of the vinblastine type are well-known compounds of the general formula:

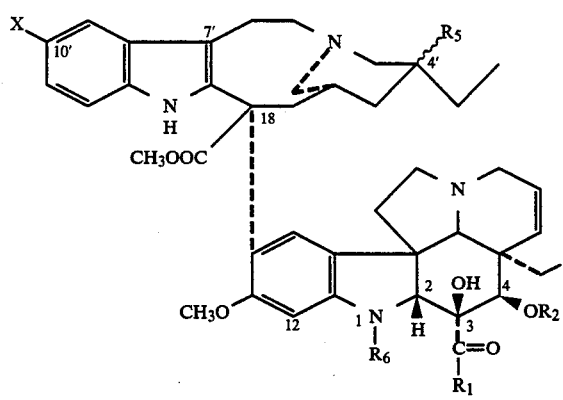

Such alkaloids include vincaleukoblastine (U.S. Pat. No. 3,097,137), leurocristine or vincristine and leurosidine (U.S. Pat. No. 3,205,220) N-desmethylvinblastine (U.S. Pat. No. 3,354,163,) vinglycinate (Belgian Pat. No. 659,112) and vindesine (Belgian Pat. No. 813,168). The latter compound is obtained by chemical modification of natural vinblastine (I, $R_1=OCH_3$, $R_2=COCH_3$, $R_5=OH$, $R_6=CH_3$, $X=H$), which is obtainable by extraction from Catharanthus roseus leaves.

Vinblastine, vincristine and vindesline are commercially available for use in human therapy, more particularly, for the treatment of leukemia and some solid tumors.

However, these drugs have been shown to possess major unfavorable side-effects. Vincristine shows neurotonic effects and vinblastine is considered to have potent bone marrow depressant effects, i.e. hematopoietic toxicity.

The mechanism of action of these drugs is believed to be similar to the mechanism which has been postulated for the antimitotic action of colchicine. In such case, these drugs would act through inhibition of the polymerisation of tubuline to give microtubules, and subsequent arrest of the cell cycle at the mitotic phase.

The utilization of 1:1 complexes of tubuline with antitumoral bisindole alkaloids has been described in Belgian Pat. No. 854,053. In some cases, lower toxicity and more efficient chemotherapeutic activity than free alkaloids was reported.

Various other chemical modifications of the vinblastine molecule have been tested. One of these modifications, vinglycinate sulphate (I, sulphate, $R_1=OCH_3$, $R_2=COCH_2N(CH_3)_2$ (Cancer Research 1967,27,221–227), has also been tested clinically but has been shown to be generally not superior to vinblastine or vincristine.

Belgian Pat. No. 813,168 discloses Veindesine ($I,R_1=NH_2$, $R_2=H$) and vinblastine carboxamide derivatives. Subsequent reports indicate that in spite of general usefulness of vindesine or 3-carboxamide 4-O-deacetyl vinblastine, they are not efficient for the treatment of mouse induced murine 1210 leukemia (C. J. Barnett et alK, J. Med. Chem. 21, 88,1978). Vindesine is currently sold on the European market (i.a. in France and Germany) and FDA registration is pending in the U.S.A.

Amino acid derivatives of vinblastine or other bisindole alkaloids have been proposed generally in Belgian Pat. Nos. 813,168 and 837,390 (corresponding to U.S. Pat. No. 4,203,898). However no specific amino acid derivatives are disclosed and consequently, no physicochemical descriptions, no specific method of preparation and no particular physicochemical properties are disclosed. It may thus be assumed that such compounds have not been actually synthetized and/or have not been tested for their antimitotic potencies, particularly in view of the statement in the disclosure at page 3, line 10 et seq. that "anti-neoplastic activity seems to be limited to very specific structures, and the chances of obtaining more active drugs by modification of these structures would seem to be correspondingly slight" (first above mentioned patent).

It has been found that the new compounds according to this invention are able to substantially delay the death of mice inoculated intravenously with P 388 and L 1210 leukemias and show important advantages over the previously described vinblastine analogs.

Vinca alkaloids generally show no activity on L 1210 leukemia. The results obtained with the new compounds of the invention indicate highly unexpected and surprizing activities on P 388 and L 1210 experimental tubors. Numerous total remissions have been observed.

The compounds of the instant invention further show other important and unexpected advantages compared to vinblastine and known analogs, especially vindesine. More particularly, the toxicities are generally more favorable when compared to vincristine or vindesine.

Among new compounds of the invention, there are some 10'-bromo substituted vinblastine derivatives.

There are only few examples of vinblastine derivatives substiuted on the aromatic nucleus of the velbanamine moiety.

European patent application No. 79400585.0 (Publication No. 10458) filed on Aug. 23, 1979 discloses however a process to prepare such mono or dihalo substituted derivatives. Halogenation, which is run in an organic solvent such as benzene or $CH_2Cl_2$, occured however at position 7' and, optionally, at position 12 of the vindoline moiety. More particularly, 7'-chloro and 12,7'-dichloro indolenine of anhydrovinblastine and 12-chloro-nor-5'-anhydrovinblastine were described.

On the other hand, microbiological transformation using a Streptomyces species afforded among isolated metabolites hydroxy-10'-vinblastine or leurosine. (Neuss et al., Helv. Chim. Acta 57, 1886, 1974; Rosazza et al., J. Natural Products 44, 478, 1981).

SUMMARY OF THE INVENTION

This invention involves a novel class of vinblastine derivatives particularly 23-oyl amino acid derivatives of vinblastine, desmethylvinblastine, vincristine, deoxyvinblastine and their O-4 deacetylated or 10'-bromo analogs, i.e. compounds of Formula I wherein $R_1$ is an amino acid ester or a peptide ester attached to the vinblastine-23-oyl type moiety through an amide linkage and their pharmaceutically acceptable salts.

In another aspect, the invention involves the preparation of novel vinblastine derivatives by hydrazinolysis of the vinblastine followed by nitrosation and coupling with an amino acid or polypeptide ester.

In still another aspect, the invention involves therapeutic methods and compositions for the treatment of cancers in mammalian species by administering to a cancer patient an effective amount of a compound of Formula I or a single 10'-brominated derivative, 10'-bromo VLB having been shown to possess quite unexpected superior activity against certain murine tumors when compared to vinblastine.

DETAILED DESCRIPTION OF THE INVENTION

The new compounds of the present invention are those of the general formula II:

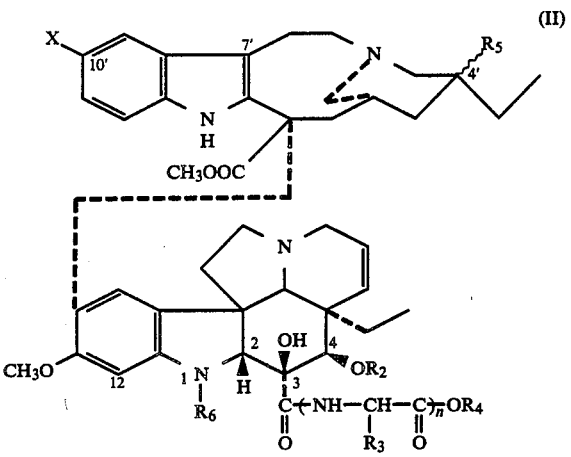

wherein $R_2$ is a hydrogen atom or $C_2$-$C_9$ acyl group, preferably acetyl; $R_3$ is a hydrogen atom, straight or branched $C_1$-$C_8$ alkyl, hydroxy-$C_1$-$C_8$-alkyl, carboxy-$C_1$-$C_8$-alkyl, amido-$C_1$-$C_8$-alkyl, amino-$C_1$-$C_8$ alkyl or hydroxyalkyl, guanadino-$C_1$-$C_8$-alkyl, sulhydryl-$C_1$-$C_8$-alkyl, methylthioethyl, benzyl, hydroxy-benzyl, or a group:

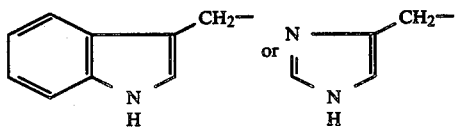

or $R_3$ together with the carbon to which it is attached and the amido nitrogen, forms an azole or hydroxy azole ring; n is an integer of from 1 to 6; and $R_4$ is a straight or branched $C_1$-$C_8$-alkyl or a α benzyl group.

—$COOR_4$ is preferably the carbethoxy or the carbomethoxy group, $R_5$ is H or OH; $R_6$ is $CH_3$, CHO or H, and X=H or Br.

In a preferred embodiment, the structural segment

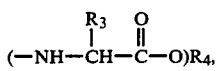

in general formula II, represents an ester derived from any of the naturally-occuring amino acids and their optical isomers of D-configuration, namely glycine, alanine, valine, leucine, isoleucine, serine, threonine, aspartic acid, glutamic acid, aspargine, glutamine, arginine, lysine, cryteine, cystine, methionine, phenylalanine, tyrosine, tryptophan, proline, histidine, hydroxylysine, hydroxyproline.

In the case of amino acids having more than one asymmetric center, both the L-allo and the D-allo forms are included.

The compounds may be designated as 3-descarbomethoxy-O-4-deacetyl vinblastine-3-carboxamide. They will however be preferably designated as N-(vinblastin-23-oyl) or N-(vincristine-23-oyl)-amino-acids derviates hereafter.

Particularly preferred amino acid ester compounds of general formula II are those wherein $R_2$ is hydrogen and the amino acid moieties are derived from one of the following amino-acids: L or D tryptophan, valine, isoleucine, leucine, phenylalanine and alanine.

Most preferred among these amino-acids are L-tryptophan, L-isoleucine and L-valine.

Particularly preferred peptide derivatives are those of formula II wherein is 2 and the amino-acids are selected from the prefrred L or D six amino acids indicated above in any sequence.

Particularly preferred vinblastine-type moeities are derived from O-4-deacetyl-vinblastine and deoxy-4'deacetyl O4-vinblastine-B, B meaning that the configuration of the ethyl group at position 4' is the one found in leurosidine.

As far as the pharmacological properties of the compounds are concerned, it is to be expected that slight variations of the structure of the peptide backbone will yield compounds of comparable potency. In particular, the presence of non-natural α-amino-acids (for example norleucine, N-monosubstituted-amino acids or α,αdialkyl-aminoacids) will provide compounds of similar activity against variety of tumors and are to be considered as included in the scope of the present invention.

The compounds of general formula II can be obtained starting from vinblastine, or a modified vinblastine, by hydrazinolysis followed by nitrosation and reaction with the appropriate amino acid ester or peptide ester, in accordance with the reaction sequence hereunder.

When the amino acid or peptide moiety contains a functional side chain $R_3$ it may be necessary to protect the functional groups according to well-known methods used in peptide chemistry. This is more particularly the case for lysine or cysteine. Protection may be achieved, depending on the nature of the amino acid, by the presence of a benzyl, trifluoro-acetyl, t-butyl, benzyloxycarbonyl, t-butoxycarbonyl or trityl radical condensed with the functional group. Other well-known protecting groups in common use in peptide chemistry may successfully be used.

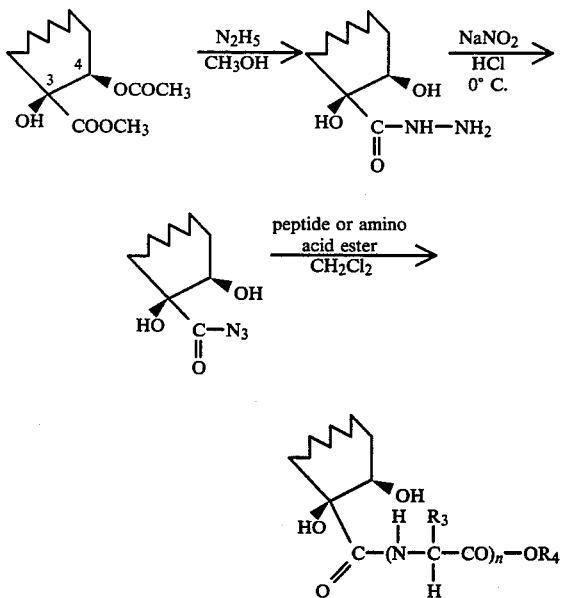

In the particular case of 4'-deoxyvinblastine derivatives, the starting product may be obtained by applying a process comprising the coupling of vindoline with catharantie N-oxide as described by Potier et al., (J. Amer. Chem. Soc. 98, 7017, 1976).

Optionaly the same alcaloid may be obtained by dehydration of vinblastine using thionyl chloride (see Belgian Pat. No. 867,255 Gedeon Richter).

In both cases, the product obtained is anhydrovinblastine which is easily catalytically reduced in methanol/$PtO_2$ or Pd on charcoal. The reduction product is 4'-deoxyvinblastine B. 4'-deoxyvinblastine A is a natural alkaloid which is fully disclosed in Neuss et al., Tetrahedron Letters 783, 1968.

Quite unexpectedly, 10'-bromovinblastine, a new vinblastine derivative, was obtained by a direct bromination reaction of vinblastine or preferably the corresponding sulphate salt. This is a selective reaction that may be run at room temperature with good yield. The bromination reagent of choice is N-bromosuccimide dissolved in trifuoroacetic acid. Other strong organic acids may be used as solvent. The reaction proceeds smoothly with 1 molar equivalent of N-bromosuccimide.

Still more surprisingly, one may also use bromine in an inert solvent such as a halogenated solvent, for example dichloromethane.

Using the abovementioned techniques, there was obtained 10'-bromovinblastine, 10'-bromo-04-deacetyl-vinblastine, 10'-bromo-vincristine and other 10'-bromo derivatives of particular interest. Reaction time at room temperature, using N-bromo reagents, varied between 12 hours and 5 days. The reactions were easily monitored by thin layer chromatography (tlc). A classical work-up of the resulting reaction mixture includes treatment with ammonia and extraction with water immiscible solvent, concentration at reduced pressure ana cristallization or chromatographic purification.

The first step of the process preferably comprises adding anhydrous hydrazine in excess to a solution of vinblastine or derivatives thereof as a base in anhydrous methanol. Generally the solution is heated in an inert atmosphere ($N_2$or Ar) for 12 to 30 hours at a temperature varying between about 30° C. and 70° C. Most preferably the temperature is maintained around 60° C., reaction time then being 24 hours. However in the particular case of deoxy-vinblatine-B derivatives, reaction times may be as long as 5 days at 55° C.

The hydrazide of 4-O-deacetyl-vinblastin-23-oic acid (e.g. I, $R_1$=NH—$NH_2$, $R_2$=H, $R_5$=OH, $R_6$=$CH_3$) is then isolated by adding water, extracting with water-immiscible solvent such as methylene chloride and concentrating under reduced pressure. The compound may be further purified by column chromatography (preferably on neutral silica).

In the case of N-formyl derivatives (for example vincristine), hydrazinolylsis will afford the deformylated (I, $R_6$=H) hydrazide.

In a second step, the hydrazide group of the modified vinblastine is transformed into an acyl azide. This transformation is best achieved by adding sodium nitrite to the hydrazide dissolved in a water-acidic methanol mixture. The acid in this mixture may be, for instance, hydrochloric acid. The reaction temperature is maintained between about 0° C. and 5° C.

After extraction with a water-immiscible aprotic solvent, preferably chloroform or methylene chloride, the organic phase is separated and partially concentrated.

The acyl azide is generally not isolated but directly added to the amino acid ester or the polypetide, or a protected derivative thereof, dissolved in a suitable solvent such as methylene chloride.

The quantity of amino acid to be used is about one to four molar equivalents of the vinblastine carboxazide.

The reaction mixture is typically maintained between about −3° C. and +5° C. for about 15 hours. Monitoring of the reaction is best achieved by thin layer chromatography. After completion of the reaction, the solvent may be removed under reduced pressure and the resulting product may be transformed into a sulphate salt or another suitable salt derived from a mineral or organic acid, by crystallization from a methanolic solution of the corresponding acid. The pure compound of the invention may be isolated and purified by conventional techniques of cristallization and chromatography.

If desired, the resulting 4-O-deacetyl modified vinblastine can be reacylated either directly to give the vinblastine derivative II wherein $R_2$ is $COCH_3$ (J. Med. Chem. 22, 391, 1979) or through the formation of the 3,4-diacetoxy derivative followed by a selective hydrolysis of the 3-acetoxy group in the position 3. The hydroxy group in $C_4$ may be, also esterified by other activated acid derivatives containing 1-9 carbon atoms.

Optionally if the resulting modified vinblastine is N-deformylated, reformylation may be achieved applying known methods (see for example Belgian Pat. No. 811,110.

Alternatively, the corresponding N-methyl vinblastine moiety may be oxidized according to known methods. Example of the latter are disclosed in Belgian Pat. No. 793,337 (hydrochloric acid, acetone) or European Pat. No. 37,289 ($H_2O_2$, $CH_3CN$, Fe($Clo_4$)$_2$).

The instant invention relates also to the pharmaceutical compositions, particularly for use in the treatment of human cancers, comprising one or more of the new bisindole alkaloids of the invention preferably in association with a pharmaceutical vehicle.

The compounds of the invention display particularly remarkable antitumor properties which may be applied with success in human cancer therapy.

They are for example, useful when used for the treatment of L 1210, P 388, gliomas, lymphosacromas and other leukemias or malignant tumors. In human medicine they may be useful for the treatment of Hodgins disease and for other solid tumors treatable with vinblastine, vincristine or vindesine. These compounds are also useful in veterinary medicine for the treatment of animals tumors.

Other therapeutical uses may also be contemplated for the new-compounds of the invention, similarly to vinblastine which may be used for treating same forms of arthritis (U.S. Pat. No. 4,208,414) or to vincristine which has been shown to be active for treating psoriasis (U.S. Pat. No. 3,749,784). The anti-viral activity of bis-indole alkaloids has also been reported.

For the treatment of experimental malignancies in animals, the chemotherapeutic activities have been tested using the corresponding sulphate salts.

In the tests reported DBA 2 female mice (Strain Charles River France) were inoculated intravenously with $10^4$ leukemic cells obtained from 7 days old P 388 or L 1210 leukemic ascites. Day 0 is the day of inoculation of the tumoral cells.

The compound of the invention (sulfate form) is then injected intravenously, dissolved in a physiological saline solution (NaCl 9/1000) either using a single injection schedule (day 1) or a three injections schedule (day 1, 2 and 3). The MST (Median Survival Time), i.e. the day when half of the animals have died is calculated after the 30th day.

The value ILS (Increased Life Span) is calculated in accordance with the following formula:

$$\% ILS = \left( \frac{MST \text{ product}}{MST \text{ control}} \times 100 \right) - 100$$

The number of surviving mice after the 30th and the 60th day is also indicated.

When the doses are too toxic, the ILS percentage may become negative, i.e. non treated mice survive longer than those having been injected the anti-tumoral substance.

Under certain circumstances, some variability of the ILS may be observed depending upon the origin of the mice (DBA$_2$ France or USA).

The results which have been obtained are compared with those obtained with vinblastine (VLB), vindesine (VDS) and vincristine (VCR) in Table I. The pharmacological superiority of the compound of the present invention is demonstrated in Tables II–XV.

In Table II, results obtained with some derivatives of natural leucine are represented.

The following compounds have been tested.
  VLE: ethyl N-(O-4-deacetyl-vinblastin-23-oyl)-L-leucinate
  VLM: methyl N-(O-4-deacetyl-vinblastin-23-oyl)-L-leucinate.

In table III, results obtained with D-leucine derivatives, namely ehtyl N-(O-4-deacetyl-vinblastin-23-oyl)-D-leucinate (VDLE) are indicated.

In table IV, results obtained with L-tryptophane derivatives are represented, namely:
  V-Trypt E: ethyl N-(O-4-deacetyl-vinblastin-23-oyl)-L-tryptophanate, MST calculated for 30 and 60 days.
  V-Trypt M: methyl N-(O-4-deacetyl-vinblastin-23-oyl)-L-tryptophanate.

In Table V, the activities observed with a derivative of ethyl tryptophanate, of absolute D configuration: ethyl N-(O-4-deacetyl-vinblastin-23-oyl)-D-tryptophanate (VD Trypt E) is indicated.

In tables VI–XI, results are indicated which have been obtained with the following compounds; respectively
  VAE: ethyl N-(O-4-deacetyl-vinblastin-23-oyl)-L-alaninate.
  VPE: ethyl N-(O-4-deacetyl-vinblastin-23-oyl)-L-phenylalaninate.
  VILE: ethyl N-(O-4-deacetyl-vinblastin-23-oyl)-L-isoleucinate.
  VILM: methyl N-(O-4-deacetyl-vinblastin-23-oyl)-L-isoleucinate.
  VVE: ethyl N-(O-4-deacetyl-vinblastin-23-oyl)-L-valinate
  V-Try E: ethyl N-(O-4-deacetyl-vinblastin-23-oyl)-L-tyrosinate
  V-Val-Trypt E: ethyl N-(O-4deacetyl-vinblastin-23-oyl)-L-valinyl-L-tryptophanate.

In table XIV results are indicated which were obtained with ethyl N-(O-4-deacetyl-4'-deoxy-vinblastin-23-oyl-B)-L-tryptophanate (deoxy-V-Trypt E).

Anti-tumor activities of 10'-bromo-vinblastine (bromo VLB) 10'-bromo-04-déacétylvinblastine (bromo DAVLB) and ethyl N-(10'-bromo-04-deacetyl vinblastin-23-oyl)-L-tryptophanate (bromo VTrypt E) are shown in table XV.

TABLE I

| doses mg/kg/day | schedule (days) | number of animals | MST max 30 days | ILS % | >30 days | >60 days |
|---|---|---|---|---|---|---|
| A. VINDESINE (VDS) | | | | | | |
| P 388 | | | | | | |
| 2 | 1 | 10 | 13.6 | 27.1 | 0 | 0 |
| 3 | 1 | 10 | 14 | 30.8 | 0 | 0 |
| 4 | 1 | 10 | 14.8 | 38.3 | 0 | 0 |
| 5 | 1 | 10 | 13.8 | 30.2 | 0 | 0 |
| 6 | 1 | 10 | 14 | 32 | 0 | 0 |
| L 1210 | | | | | | |
| 3 | 1 | 20 | 8.7 | 5 | 0 | 0 |
| B. VINCRISTINE (VCR) | | | | | | |
| P 388 | | | | | | |
| 0.5 | 1 | 10 | 11.56 | 4 | 0 | 0 |
| 1 | 1 | 19 | 12.32 | 15 | 0 | 0 |
| 1.5 | 1 | 20 | 12.78 | 19 | 0 | 0 |
| 2 | 1 | 10 | 6 | −46 | 0 | 0 |
| L 1210 | | | | | | |
| 0.5 | 1 | 10 | 7.56 | 1 | 0 | 0 |
| 1 | 1 | 20 | 7.91 | 5 | 0 | 0 |
| 1.5 | 1 | 20 | 8.38 | 12 | 0 | 0 |
| 2 | 1 | 10 | 8.67 | 16 | 0 | 0 |
| C. VINBLASTINE (VLB) | | | | | | |
| P 388: | | | | | | |
| 4 | 1 | 10 | 14.6 | 36.4 | 0 | 0 |
| 6 | 1 | 10 | 15.6 | 45.8 | 0 | 0 |
| 8 | 1 | 9 | 18.5 | 72.9 | 0 | 0 |

TABLE II

| doses mg/kg/day | schedule (days) | number of animals | MST max 30 days | ILS % | >30 days | >60 days |
|---|---|---|---|---|---|---|
| DERIVATIVES OF NATURAL LEUCINE | | | | | | |
| A. VLE | | | | | | |
| P 388: | | | | | | |
| 20 | 1 | 10 | 16 | 52.4 | 2 | 1 |

TABLE II-continued

DERIVATIVES OF NATURAL LEUCINE

| doses mg/kg/day | schedule (days) | number of animals | MST max 30 days | ILS % | >30 days | >60 days |
|---|---|---|---|---|---|---|
| 22 | 1 | 10 | 20 | 90.5 | 4 | 1 |
| 24 | 1 | 20 | 18 | 65 | 2 | 0 |
| 26 | 1 | 10 | 17.5 | 53.5 | 1 | 0 |
| 28 | 1 | 10 | 19.6 | 71.9 | 1 | 1 |
| 30 | 1 | 10 | 21 | 84.2 | 2 | 1 |
| 34 | 1 | 10 | 6 | −48 | 2 | 1 |
| 36 | 1 | 10 | 5.4 | −53 | 1 | 1 |
| 5 | 1.2.3 | 9 | 14.5 | 25 | 0 | 0 |
| 6 | 1.2.3 | 10 | 15 | 29.3 | 0 | 0 |
| 7 | 1.2.3 | 10 | 14.2 | 24.6 | 0 | 0 |
| 9 | 1.2.3 | 10 | 5 | −56 | 1 | 1 |
| 12 | 1.2.3 | 9 | 4.8 | −59 | 0 | 0 |

B. VLM
P 388:

| doses mg/kg/day | schedule (days) | number of animals | MST max 30 days | ILS % | >30 days | >60 days |
|---|---|---|---|---|---|---|
| 10 | 1 | 20 | 16.7 | 41 | 2 | 1 |
| 10.5 | 1 | 10 | 16.4 | 53.3 | 0 | 0 |
| 11 | 1 | 19 | 17.7 | 51 | 2 | 1 |
| 11.5 | 1 | 10 | 16.8 | 57 | 0 | 0 |
| 12 | 1 | 20 | 17.5 | 49 | 3 | 2 |
| 12.5 | 1 | 30 | 17.3 | 49 | 8 | 3 |
| 13 | 1 | 20 | 20.5 | 74 | 7 | 5 |
| 15 | 1 | 10 | 18 | 55.2 | 4 | 1 |

L 1210:

| | | | | | | |
|---|---|---|---|---|---|---|
| 10.5 | 1 | 10 | 10.6 | 24.7 | 0 | 0 |
| 11.5 | 1 | 10 | 10.8 | 27 | 0 | 0 |
| 12.5 | 1 | 10 | 10 | 17.6 | 0 | 0 |

TABLE III

A. VDLE

| mg/kg/day | schedule (days) | number of animals | MST max 30 days | ILS % | >30 days | >60 days |
|---|---|---|---|---|---|---|
| | | | P 388: | | | |
| 6 | 1 | 10 | 14.7 | 26.7 | 0 | 0 |
| 8 | 1 | 10 | 17 | 46.5 | 2 | 1 |
| 10 | 1 | 20 | 28.5 | 146 | 9 | 2 |
| 12.5 | 1 | 10 | 30 | 145.9 | 6 | 3 |
| | | | L 1210 | | | |
| 9 | 1 | 10 | 10.8 | 27 | 0 | 0 |
| 10 | 1 | 10 | 11 | 29.4 | 0 | 0 |

TABLE IV

A. V Trypt E

| doses mg/kg/day | schedule (days) | number of animals | MST max 30 days | ILS % | >30 days | >60 days |
|---|---|---|---|---|---|---|
| | | | P 388: | | | |
| 20 | 1 | 10 | 11.4 | 43.9 | 0 | 0 |
| 40 | 1 | 10 | 17 | 58.8 | 5 | 4 |
| 50 | 1 | 20 | 24.5 | 117 | 9 | 5 |
| 55 | 1 | 60 | 41 | 279 | 39 | 25 |
| 60 | 1 | 100 | 33 | 202 | 57 | 36 |
| 65 | 1 | 29 | 22.75 | 114 | 13 | 9 |
| 70 | 1 | 20 | 6.5 | −39 | 8 | 5 |
| | | | L 1210: | | | |
| 55 | 1 | 30 | 11.8 | 56 | 0 | 0 |
| 60 | 1 | 30 | 12.5 | 65 | 2 | 2 |
| 65 | 1 | 30 | 12 | 62 | 0 | 0 |
| 70 | 1 | 10 | 12.3 | 61.8 | 1 | 1 |

| doses mg/kg/day | schedule (days) | number of animals | MST max 60 days | ILS % | >30 days | >60 days |
|---|---|---|---|---|---|---|
| | | | P 388 (max 60 days): | | | |
| 55 | 1 | 30 | 60 | 457 | 28 | 16 |
| 60 | 1 | 60 | 36 | 224 | 52 | 24 |

B. V Trypt M

TABLE IV-continued

| doses mg/kg/day | schedule (days) | number of animals | MST max 30 days | ILS % | >30 days | >60 days |
|---|---|---|---|---|---|---|
| | | | P 388: | | | |
| 30 | 1 | 10 | 15 | 33.9 | 0 | 0 |
| 40 | 1 | 10 | 16 | 42.8 | 0 | 0 |
| 50 | 1 | 10 | 23.5 | 199.8 | 1 | 0 |
| 60 | 1 | 20 | 26 | 140 | 7 | 2 |
| 70 | 1 | 10 | 26 | 145.3 | 5 | |
| | | | 1210 | | | |
| 50 | 1 | 10 | 11.5 | 47.4 | 0 | 0 |
| 55 | 1 | 10 | 12.5 | 60.2 | 0 | 0 |

TABLE V

VD Trypt E

| doses mg/kg/day | schedule (days) | number of animals | MST max 30 days | ILS % | >30 days | >60 days |
|---|---|---|---|---|---|---|
| | | | P 388 | | | |
| 20 | 1 | 10 | 13.3 | 18.7 | 0 | 0 |
| 30 | 1 | 10 | 15.8 | 41.4 | 1 | 0 |
| 40 | 1 | 20 | 16.5 | 52 | 1 | 0 |
| 50 | 1 | 10 | 22 | 107.5 | 1 | 0 |
| 60 | 1 | 10 | 4.4 | −60.7 | 1 | 0 |
| | | | L 1210 | | | |
| 40 | 1 | 10 | 9.5 | 21.8 | 0 | 0 |
| 45 | 1 | 10 | 10.5 | 34.6 | 0 | 0 |

TABLE VI

VAE

| doses mg/kg/day | schedule (days) | number of animals | MST max 30 days | ILS % | >30 days | >60 days |
|---|---|---|---|---|---|---|
| | | | P 388: | | | |
| 5 | 1 | 10 | 14.8 | 27.6 | 0 | 0 |
| 10 | 1 | 10 | 16.3 | 40.5 | 0 | 0 |
| 12.5 | 1 | 19 | 16.2 | 44 | 1 | 1 |
| 15 | 1 | 20 | 17 | 46 | 5 | 4 |
| 25 | 1 | 10 | 19 | 63.8 | 2 | 1 |
| | | | L 1210: | | | |
| 12.5 | 1 | 20 | 10.4 | 48 | 0 | 0 |

TABLE VII

A. VPE

| doses mg/kg/day | schedule (days) | number of animals | MST max 30 days | ILS % | >30 days | >60 days |
|---|---|---|---|---|---|---|
| | | | P 388: | | | |
| 10 | 1 | 10 | 13 | 12.1 | 0 | 0 |
| 20 | 1 | 10 | 14.4 | 24.1 | 0 | 0 |
| 40 | 1 | 10 | 30 | 158.6 | 7 | 7 |
| 50 | 1 | 30 | 13.6 | 26 | 10 | 7 |
| 55 | 1 | 10 | 14.6 | 36.4 | 1 | 0 |
| | | | L 1210 | | | |
| 70 | 1 | 20 | 8.7 | 13 | 0 | 0 |
| 75 | 1 | 10 | 9.5 | 25 | 0 | 0 |

TABLE VIII

| doses mg/kg/day | schedule (days) | number of animals | MST max 30 days | ILS % | >30 days | >60 days |
|---|---|---|---|---|---|---|
| | | | VILE | | | |
| | | | P 388: | | | |
| 8 | 1 | 30 | 30 | 172 | 20 | 2 |
| 9 | 1 | 20 | 30 | 179 | 12 | |
| | | | L 1210 | | | |

TABLE VIII-continued

| doses mg/kg/day | schedule (days) | number of animals | MST max 30 days | ILS % | >30 days | >60 days |
|---|---|---|---|---|---|---|
| 8 | 1 | 20 | 11.57 | 58 | 0 | 0 |
| 9 | 1 | 10 | 12.8 | 68.4 | 0 | 0 |
| VILM P 388: | | | | | | |
| 3 | 1 | 10 | 16.4 | 41.3 | 0 | 0 |
| 5 | 1 | 29 | 18.2 | 68 | 8 | 3 |
| 6 | 1 | 69 | 23.4 | 115 | 25 | 6 |
| 7 | 1 | 30 | 30 | 177 | 16 | 5 |
| 9 | 1 | 10 | 6 | −48.3 | 4 | 4 |
| L 1210 | | | | | | |
| 6 | 1 | 29 | 11.2 | 60 | 0 | 0 |

TABLE IX

VVE

| doses mg/kg/day | schedule (days) | number of animals | MST max 30 days | ILS % | 30 days | 60 days |
|---|---|---|---|---|---|---|
| P 388: | | | | | | |
| 5 | 1 | 10 | 13.6 | 17.2 | 0 | 0 |
| 10 | 1 | 10 | 17.8 | 53.4 | 0 | 0 |
| 12.5 | 1 | 10 | 21 | 82.6 | 2 | 0 |
| 14 | 1 | 20 | 21 | 98 | 3 | |
| 15 | 1 | 39 | 23.5 | 107 | 14 | 4 |
| 17.5 | 1 | 9 | 8.4 | −22.2 | 0 | 0 |
| L 1210 | | | | | | |
| 15 | 1 | 19 | 11.4 | 61.9 | 0 | 0 |

TABLE X

V Tyr E

| doses mg/kg/day | schedule (days) | number of animals | MST max 30 days | ILS % | 30 days | 60 days |
|---|---|---|---|---|---|---|
| P 388 | | | | | | |
| 20 | 1 | 10 | 13.9 | 29.9 | 0 | 0 |
| 40 | 1 | 10 | 16.4 | 53.3 | 1 | 1 |
| 50 | 1 | 10 | 16 | 49.5 | 1 | 1 |
| 60 | 1 | 10 | 16 | 49.5 | 3 | 2 |
| 70 | 1 | 10 | 5.4 | −49.5 | 0 | 0 |

TABLE XI

V—Val—Trypt E

| doses mg/kg/day | schedule (days) | number of animals | MST max 30 days | ILS % | >30 days | >60 days |
|---|---|---|---|---|---|---|
| P 388: | | | | | | |
| 15 | 1 | 10 | 26 | 132.1 | 3 | 0 |
| 25 | 1 | 10 | 27.5 | 145.5 | 3 | 2 |
| 35 | 1 | 19 | 27.5 | 154 | 8 | 4 |
| 45 | 1 | 20 | 30 | 180 | 13 | 7 |
| 50 | 1 | 19 | 27.5 | 149 | 9 | 7 |

TABLE XII intraperitoneal injected P 388
BDF 1 Charles River France female

| PRODUCT | DOSE | SCHEDULE | NO OF ANIMALS | MST | ILS | 30 DAYS |
|---|---|---|---|---|---|---|
| VCR | 2.7 | 1 | 11 | 15.6 | 64.2 | 0 |
| V-Trp-E | 50 | 1 | 10 | 22 | 131.6 | 1 |
| V-Trp-E | 60 | 1 | 10 | 31 | 226 | 6 |
| V-Trp-E | 80 | 1 | 10 | 21.5 | 126.3 | 0 |

Activity of V-Trp-E and VCR on P 388 leukemia i.p. inoculated in BDF 1 female mice which have recieved $10^6$ leukemia cells at day 0. At day 1, the active products are i.p. administered at the given doses.

Lewis Lung Carcinoma (3LL)

$1.1 \times 10^6$ tumoral cells are intramuscularly inoculated in the right hind leg of C57B1 female mice.

The drugs are administered intravenously in a schedule of 3 injections.

The animals are killed the 23rd day after the inoculation. The weight of the primary tumor is measured in grams; the pulmonary metastasis are computed and their diameter has been measured. The weight of metastasis has been evaluated by assuming that they are spheres of density equal to 1; the number of mice without metastasis has also been indicated.

The results appear in Table XIII. The three products show an activity on the primary tumor.

The medium weight of the metastasis, their mean number as well as the number of mice without metastasis are indicated and allow an evaluation of the antimetastasic activity of the administrated anti-tumoral compounds.

TABLE XIII

| Product | Dose mg/kg/day | Number of dissected mice | Weight of the tumor (g) X | σ | Weight of metastasis (mg) X | σ | Mean number of metastasis | | Number of mice without metastasis |
|---|---|---|---|---|---|---|---|---|---|
| — | — | 20 | 9.64 | 0.916 | 27.61 | 54.53 | 28.4 | 15.22 | 0 |
| VDS | 2.5 | 22 | 5.72 | 0.698 | 0.40 | 0.91 | 13.68 | 7.49 | 0 |
| Vtryp E | 50 | 21 | 4.83 | 0.868 | 0.047 | 0.038 | 4.58 | 2.83 | 2 |

TABLE XIV

Deoxy V—Trypt E

| doses mg/kg day | schedule (days) | number of animals | MST max 30 days | ILS % | 30 days | 60 days |
|---|---|---|---|---|---|---|
| P 388 | | | | | | |
| 4 | 1 | 5 | 15.6 | 56 | 0 | 0 |
| 8 | 1 | 5 | 5.8 | −42 | 0 | 0 |
| 30 | 1 | 10 | 16.5 | 58.7 | 0 | 0 |
| 40 | 1 | 15 | 30 | 191 | 67 | 53 |
| 50 | 1 | 15 | 30 | 191 | 87 | 73.3 |
| 55 | 1 | 10 | 30 | 212 | 80 | 60 |
| 60 | 1 | 10 | 30 | 212 | 90 | 90 |
| L 1210 | | | | | | |
| 8 | 1 | 10 | 10.4 | 57.6 | 0 | 0 |
| 19 | 1 | 10 | 5.8 | −21.6 | 0 | 0 |
| 50 | 1 | 10 | 11.2 | 70 | 0 | 0 |

TABLE XV

Bromo derivatives

| Product | doses mg/kg day | number of animals | MST day 30 | ILS | % surv. day 30 | % surv. day 60 |
|---|---|---|---|---|---|---|
| P 388 | | | | | | |
| Bromo- | 2 | 10 | 12.3 | 6.9 | 10 | 10 |

TABLE XV-continued

| | | Bromo derivatives | | | | |
|---|---|---|---|---|---|---|
| Product | doses mg/kg day | number of animals | MST day 30 | ILS | % surv. day 30 | % surv. day 60 |
| DAVBL | 4 | 8 | 14.6 | 26.9 | 0 | 0 |
| | 5 | 30 | 16 | 57 | 7 | 0 |
| | 6 | 40 | 19 | 76 | 8 | 0 |
| | 7 | 20 | 16 | 49 | 0 | 0 |
| | 8 | 30 | 17.7 | 65 | 13 | 0 |
| | 12.5 | 10 | 5.4 | −53 | 0 | 0 |
| Bromo VLB | 5 | 30 | 25.7 | 152 | 37 | 13.3 |
| | 6 | 30 | 24.5 | 141 | 47 | 13.3 |
| | 7 | 10 | 27 | 160 | 40 | 10 |
| | 10 | 10 | 5.8 | −44.2 | 20 | 20 |
| Bromo VTrpE | 10 | 10 | 10.5 | 10.5 | 0 | 0 |
| | 20 | 10 | 11 | 15.8 | 0 | 0 |
| | 40 | 10 | 13.6 | 43.2 | 0 | 0 |
| | 45 | 10 | 15.5 | 63.2 | 0 | 0 |
| | 55 | 10 | 16 | 53.8 | 10 | 10 |
| | 65 | 20 | 23 | 122 | 40 | 20 |
| | 70 | 10 | 21 | 121 | 20 | 20 |
| | 75 | 10 | 21 | 102 | 50 | 50 |
| | | L 1210 | | | | |
| Bromo DAVBL | 5 | 10 | 9.8 | 48.5 | 0 | 0 |
| | 6 | 10 | 10 | 17.6 | 0 | 0 |
| | 7 | 10 | 10.2 | 20 | 0 | 0 |
| Bromo VLB | 5 | 20 | 12.3 | 73 | 0 | 0 |
| | 6 | 10 | 12.5 | 64.5 | 0 | 0 |
| | 7 | 10 | 7 | −6.7 | 0 | 0 |
| | 10 | 10 | 5.5 | −26.7 | 0 | 0 |

The antitumoral activities of Tables I–XIV confirm the unexpected efficiency of the amino-acid derivatives of the present invention. Most of the compounds appear to be superior to vindesine for i.p. and i.v. inoculated tumors. The exceptional activity of these compounds on L 1210 tumors has been demonstrated. Table XV shows that results obtained with 10'-bromo derivatives are also encouraging. Moreover 10'bromovinblastine seems to be generally more active than vinblastine itself, rendering it a suitable candidate for further evaluation as a clinically active agent.

It may be worth mentioning that among experimental tumors presently available, L 1210 leukemia is recognized as being the experimental tumor which is the most significant for the selection of anti-tumor drugs for humans.

In Table XIII, the anti-metastasic tests show that the VLB-Trypt-E derivative is very superior to vindesine. The efficiency on a primary tumor is further comparable to vindesine.

The outstanding activity of the ethyl N-(deacetyl-O-4-vinblastin-23-oyl) tryptophanate sulphate which gives a ILS after 60 days (P 388) of 457% with half of the mice surviving more, should be mentioned. The optimal dose is about 60 mg.

Generally speaking, the compounds of the invention appeared highly less toxic than Vinca alkaloids presently used in anti-cancerous therapy. The lethal dose 50 ($LD_{50}$) of LVE has been determined on $CD_1$ female mice of the Charles River strain having a less than 24 g weight.

The Litchfield and Willcoxon evaluation method gives a $LD_{50}$ of 32 mg/kg.

Corresponding doses for vinblastine and vindesine are 24 mg/kg and about 11 mg/kg, respectively. As opposed to vinblastine, the absence of hepatic toxicity at doses of 20 to 40 mg/kg has been observed.

The acute toxicities of V-TRp-E and VILE have also been determined on NMRI female mice. The values which have been obtained 100.8 mg/kg and 17.7 mg/kg for V-Trp-E and VILE respectively, are to be compared with the corresponding values of 27.4 and 13.8 mg/kg for vinblastine and vindesine, respectively. V-Trp-E is thus clearly less toxic than VLB or VDS. It is also true for deoxy-V-Trypt E which has been shown to be less toxic than the corresponding non-conjugate derivative ($LD_{50}$ 91 mg/kg compared to 20 mg/kg for deoxyvinblastine-B).

First human clinical trials with V-Trypt E confirm the low toxicity of this new anti-tumor agent compared with other vinca alkaloids.

In utilizing the vinblastinoyl amino acid derivatives as antine oplastic agents, either the parental or the oral route of administration may be employed. For oral dosage, a suitable quantity of formula II is mixed in an excipient and the mixture placed in capsules or compressed into tablet in assocation with the usual binders. However, for their therapeutical uses, compounds of the invention, possibly in the lyophilized form, are preferably administered by parenteral route, dissolved in a pharmaceutically acceptable carrier either in the form of a base or of a pharmaceutically acceptable acid addition salt. A physiological water and other saline solutions buffered, for instance, with a phosphate are appropriate solvents.

Any of the acids generally employed in preparing pharmaceutically acceptable salts may be used, such as, for example, salts with mineral acids, e.g. hydrochloric, sulfuric, orthophosphoric, etc., or salts with organic acids, e.g. alkanoic acids, citric, benzene sulfonic, toluene sulfonic, methane-sulfonic, tartric, oxalic, lactic etc.

In general, the compounds can be used in human therapy in an anlogous manner to the techniques and limitations in use for other Vinca alkaloids.

General method for preparing N-(deacetyl-O-4-vinblastine-23-oyl) amino-acid derivatives 1 g (1.3 $10^{-3}$ mol) of 3-decarbomethyl-O-4 deacetyl-vinblastin-3-carbox-hydrazide was dissolved in 23 ml anhydrous methanol and 74 ml HCl 1N. The solution was then cooled at −10° C. and 207 g sodium nitrite was added in one batch.

The mixture was kept for 10–30 minutes at 0° C. After monitoring by thin layer chromatography (t.l.c.) the pH of the mixture was adjusted to 8.5 at −10° C. by addition of a saturated solution of sodium bicarbonate.

The alkaline solution was extracted at 0° C. by a volume of methylene chloride equal to its own volume, till a negative Meyer reaction was obtained on the aqueous phase. The organic phases were combined, dried on $Na_2SO_4$, and filtrated at 0° C.

1.43 $10^{-3}$ mol (1.1. equivalent) of the intended amino-acid was added and the solution was concentrated under reduced pressure until a volume of about 4 ml is obtaied.

This solution was kept for 24–48 hours at 4° C. The evolution of the reaction was monitored by thin layer chromatography. The solvent was completely removed and 1.05 g of dry compound was obtained, said compound appearing as a single spot in t.l.c. (thin layer chromatography).

Purification

The dried product above was purified in a silica gel column, the elution agent being a mixture of ether-ammonia saturated methanol 96%+4%.

Fractions of 10 ml are collected and tested by t.l.c. The used developer was ninhydrine (amino-acids) or ceric (alkaloids).

When the excess amino-acid has undergone elution (ninhydrine-), more elution agent is used before switching to a mixture 92%-8%.

The amino-acid derivative of the alkaloids was then collected (ceric +).

Identical fractions were combined, dry evaporated (rotavapor), dissolved in methylene chloride, dried on $Na_2SO_4$, filtrated and evaporated to dryness. The foam which was obtained was the amino-acid derivative of the dimeric alkaloid, of which physico-chemical properties will be determined on aliquot parts. The remaining will be directly converted into a sulphate. Yields of the base of the various compounds are only indicative and may be improved.

Preparation of the sulphate

The amorphous base (foam) is dissolved in 20 times its weight of ethanol.

To this solution, very slowly and under fast stirring, two equivalents of sulfuric acid are added as a solution 2% sulfuric acid/98% anhydrous ethanol. (0.484 equivalent/liter). After two equivalents have been added, and ½ hour of stirring, concentration under reduced pressure takes place. By adding sulfuric ether, under fast stirring, the sulphate of the initial compound precipitates. After filtration and drying under reduced pressure at 10° C., the desired sulphate derivative is obtained, ready for use.

The numbering of the description of the NMR spectra in the following examples is inspired by the one proposed by Le Men end Taylor for derivatives of the aspidospermidine type (Experientia 21,508,1965).

EXAMPLE 1

Preparation of vinblastine (VLB) base

To a solution of 1.5 g VLB sulphate ($1.65.10^{-3}$ nol) in 15 ml distilled water, under violent stirring, 15 ml methylene chloride and 1.5 ml conc. ammonia was successively added. After 5 minutes the mixture was decanted and the aqueous phase further extracted by 3×15 ml methylene chloride. The combined organic phases were washed by 2×40 ml deionized water, dried on $Na_2SO_4$ and dry evaporated on rotavapor. 1.32 g of VLB base (99%) was obtained.

Preparation of 3-decarbomethoxy-O-4-deacetyl-vinblastin-3-carbohydrazide (VLH)

To a solution of 1 g vinblastine base ($1.23\ 10^{-3}$ nol) dissolved in 7 ml anhydrous ethanol, 14 ml anhydrous hydrazine and 7 ml anhydrous ethanol was added. The reaction mixture was then heated at 60° C. during 24 hours.

After cooling, 28 ml NaCl saturated water was added and extraction with the same volume of methylene chloride until a negative Meyers reaction is obtained on the acidified aqueous phase. The combined organic phases were dried with $MgSO_4$ and evaporated to dryness under reduced pressure.

The hydrazide which is obtained with a 88% yield (0.706 g) produced a single spot by t.l.c.

EXAMPLE 2

Preparation of ethyl N-(O-4-deacetyl-vinblastin-23-oyl)-L-leucinate (VLE)

To a solution of 275 mg ($3.58\ 10^{-4}$ mol) of O-4-deacetyl-vinblastine hydrazide in 7 ml anhydrous methanol and 20.5 ml 1N HCl, after cooling the solution at 0° C., there was added 58 mg of sodium nitrite. After stirring for 25 minutes, the pH was adjusted to 8.5 by addition of an appropriate amount of a solution of 5% $NaHCO_3$. The azide which has been formed was extracted with methylene chloride. The organic phase was dried over $MgSO_4$ and filtrated. 68.4 mg ethyl L-leucinate ($4.29\ 10^{-4}$ mol) was added and the solution was concentrated under reduced pressure to about 4 ml. The solution was allowed to stand in a refrigerator for 24 hours.

The reaction being then complete, 50 ml methylene chloride was added and the solution washed several timesw with volumes of deionized water equal to the volume of the solution and one time with a NaCl saturated solution.

The combined organic phases were dried on $MgSO_4$, filtrated and evaporated to dryness.

300 mg of crude product were thus obtained to which 0.035 g $H_2SO_4$ in solution in 1 ml anhydrous methanol were added.

The salt which was obtained was precipitated by ether and the precipitate was washed 10 times with 50 ml anhydrous sulfuric ether.

183 mg (57%) of the product are thus obtained which is substantially pure and containing no ethyl leucinate.

After freeing of the bases, they may undergo a silica gel chromatography (10 g $SiO_2$) and elution with 50 ml ether MeOH—$NH_3$ sat (92%/8% and then 250 ml ether/MeOH—$NH_3$ sat (85%/15%). VLE is obtained as head of the second eluate. 49% of VLE i.e. 152 mg base were thus collected.

Physico-chemical properties of VLE

Melting point: 169° C.

$[\alpha]D_{c=0.35}^{CHCl_3}$: 60°.

UV spectrum (MeOH, λ max, nm, logε): 221 (4.62); 267 (4.15); 287 (4.02); 295 (3.99).

IR spectrum (KBr, $cm^{-1}$): 3470, 2960, 2880, 1735, 1665, 1610.

Mass spectrum (m/e, %): 924 (6) $M^+ +28$; 910 (56) $M^+ +14$; 897 (62); 896 (100); 865 (25); 938 (68); 772 (19); 709 (25); 651 (43); 571 (69).

NMR spectrum ($H^1$, $CDCl_3$, ppm, 360 MHz): 9.66 (1H, bs, $C^{16}$—OH); 8.20 (1H,s,N'αH); 7.52 (1H,d); 7.15 (3H,m); 6.56 (1H,s,$C^9$—H); 6.05 (1H,s,$C^{12}$—H); 5.86 (1H,dd,$C^{14}$—H, J 14-15-12 J14-3-3.6; 5.78 (1H,d,$C^{15}$—H); 4.69 (1H,m,CH(NHR)CO—); 4.2 (2H,q,$OCH_2$ $CH_3$); 4.18 (1H,t,$C^{17}$—H); 3.77 (3H,s,$\overline{OCH_3}$); 3.66 (3H,s,$OCH_3$); 3.47 (1H,s,$C_5$—H); 2.77 (3H,s,$N^\alpha$—$CH_3$); 0.92 (12H,m,—$C^{18}H_3$+$C^{18'}H_3$+isopropyl).

EXAMPLE 3

Methyl-N-(O-4-deacetyl-vinblastin-23-oyl)-L-leucinate (VLM)

Following the general procedure at page 35 VLM was obtained with a 68% yield.

Physico chemical properties of VLM

Melting point: ~172° C.

$[\alpha]D_{c=0.27}^{CHCl_3}$: ~67°.

U V Spectrum (CH$_3$OH, λ max, nm, log ε): 220 (4.61); 267 (4.15); 287 (4.03); 294 (3.98).

I R Spectrum (KBr, cm$^{-1}$): 3475; 2960; 2880; 1740; 1680; 1615.

Mass spectrum (m/e, %): 910(25) M$^+$+28; 896(78) M$^+$+14; 883(26) M$^+$+1; 882(36) M$^+$; 850(29); 836(41); 822(100); 708(15); 681(56); 650(78); 570(70).

N M R spectrum (CDCl$_3$, ppm, 60 MHz): 9.21 (1H,s,C$^{16}$—OH); 8.1 (1H,s,N'$^\alpha$—H); 7.53 (1H,m); 7.23 (3H,m); 6.63 (1H,s,C$^9$—H); 6.13 (1H,s,C$^{12}$—H); 5.86 (2H,m,C$^{14}$—H+C$^{15}$—H); 3.83 (3H,s, —OCH$_3$); 3.80 (3H,s, —COOCH$_3$); 3.63 (3H,s,—OCH$_3$); 2.8 (3H,s,—N$^\alpha$—CH$_3$); 0.96 (12H,m, C$^{18}$H$_3$+C$^{18'}$H$_3$+isopropyl).

EXAMPLE 4 n-Butyl N-(O-4-deacetyl-vinblastin-23-oyl)-L-leucinate (VLn-But)

Following the general procedure at page 35, VLn-But was obtained with a 58% yield.

Physico chemical properties of VLn-But

Melting point: ~158° C.

[α]D$_{c=0.26}^{CHCl3}$: ~74°.

U V spectrum (CH$_3$OH, λ max, nm, log ε): 220 (4.66); 266 (4.21); 289 (4.08); 298 (4.03).

I R spectrum (KBr, cm$^{-1}$): 3470, 2960, 2880, 1740, 1670, 1615.

Mass spectrum (m/e, %): 925(5) M$^+$+28; 938(31) M$^+$+14; 924(12) M$^+$; 923(15 M$^+$−1; 891(13); 863(36); 835(5); 821(11); 708(33); 650(81); 570(100).

N M R spectrum (CDCl$_3$, ppm, 60 MHz): 9.6 (1H,s,C$^{16}$—OH); 8.06 (1H,s,N'$^\alpha$—H); 7.5 (1H,m); 7.2 (3H,m); 6.63 (1H,s,C$^9$—H); 6.1 (1H,s,C$^{12}$—H) 5.86 (2H,m,C$^{14}$—H+C$^{15}$—H); 4.2 (2H,t,—COO—CH$_2$); 3.83 (3H,s,—OCH$_3$); 3.63 (3H,s,—OCH$_3$); 2.8 (3H,s,—N—CH$_3$); 1 (15H,m,—C$^{18'}$H$_3$+C$^{18}$H$_3$; CH$_3$ butyl; CH$_3$ isopropyl).

EXAMPLE 5

Octyl N-(O-4-deacetyl-vinblastin-23-oyl)-L-leucinate (VL-octyl)

Following the general procedure at page 35 VL-octyl was obtained with a 48% yield.

Physico chemical properties of VL-Octyl

Melting point: ~145° C.

[α]D$_{c=0.33}^{CHCl3}$: ~20°.

UV spectrum (CH$_3$OH, λ max, nm, log ε) : 8.62 mg/l; 217 (4.69; 265 (4.14); 289 (4.01); 295 (3.95).

IR spectrum (KBr, cm$^{-1}$) : 3460; 2940; 2920; 2870; 1735; 1665; 1610; 1500; 1455.

NMR spectrum (CDCl$_3$, ppm,60 MHz): 9.6 (1H, s,C$^{16}$—OH); 8.1 (1H,s,N'—H); 7.55 (1H,m); 7.23 (3H,m) 6.5 (1H,s,C$^9$—H); 6.12 (1H,s,C$^{12}$—H); 5.90 (2H,m,C$^{14}$—H+C$^{15}$—H) 4.2 (2H,t,—O—CH$_2$—Oct; 1H,d,C$^{17}$—H); 3.83 (3H,s,—COOCH$_3$); 3.67 (3H,s,—OCH$_3$); 3.56 (1H,s,C$^5$—H); 2.83 (3H,s,N—CH$_3$); 1.33 (10H, m, massif octyl+CH$_2^{19'}$+CH$_2^{19}$); 1 (15H,m,massif octyl+CH$_3^{18}$+CH$_3^{18'}$).

EXAMPLE 6

Ethyl N-(O-4-deacetyl-vinblastin-23-oyl)-D-leucinate (VDLE)

Following the general procedure at page 35 VDLE was obtained with a 74% yield.

Physico-chemical properties of VDLE

Melting point: ~181° C.

[α]D$_{c=0.28}^{CHCl3}$: ~70°.

UV spectrum (methanol, λ max, nm, log ε): 220 (4.67); 226 (4.20); 288 (4.11); 295 (4.02).

IR spectrum (KBr, cm$^{-1}$): 3460; 2960; 2880; 1735; 1665; 1605.

Mass spectrum (m/e %): 924(14) M$^{30}$ +28; 910(32); M$^+$+14; 897(38) M$^+$+1; 896(66) M$^+$; 863(28); 835(43); 709(43); 651(81); 570(100).

NMR spectrum (CDCl$_3$,ppm,60 MHz): 9.6 (1H, s,C$^{16}$—OH); 8.16 (1H,s,N'$^\alpha$—H); 7.66 (1H,m); 7.26 (3H,m); 6.7 (1H,s,C$^9$—H); 6.16 (1H,s,C$^{12}$—H); 5.90 (2H,mC$^{14}$—H+C$^{15}$—H); 4.26 (2H,q,—COOCH$_2$); 3.83 (3H,s,—OCH$_3$); 3.66 (3H,s,—OCH$_3$); 2.90 (3H,s,—N$^\alpha$—CH$_3$); 1.3 (3H,t,—(COOCH$_2$)—CH$_3$; 096 (12H,m,C$^{18'}$H$_3$+C$^{18}$H$_3$+isopropyl).

EXAMPLE 7

Ethyl N-(O-4-deacetyl-viblastrin-23-oyl)-L-serinate (VSE)

Following the general procedure at page 35 VSE was obtained with a 35% yield.

Physico-chemical properties of VSE

[α]D$_{c=0.7}^{CHCl3}$: ~65°.

UV spectrum MeOH, λ max, nm, log ε): 215 (4.76); 266 (4.31); 288 (4.20); 297 (4.15).

IR spectrum (CHCl$_3$, cm$^{-1}$): 3460; 3400; 2965; 2935; 2880; 1730; 1665; 1605.

NMR spectrum (CDCl$_3$, ppm,60 MHz) : 8.13 (1H,s,N$^{\alpha'}$—H); 7.9 (1H,d,—OH); 7.52 (1H,m); 7.20 (3H,m); 6.63 (1H,s,C$^9$—H); 6.1 (1H,s,C$^{12}$—H); 5.9 (2H,m C$^{14}$—H+C$^{15}$—H 4.3 (2H,g,—COO—CH$_2$—); 3.83 (3H,s,—OCH$_3$); 3.66 (3H,s,—OCH$_3$); 2.67 (3H,s,—N$^\alpha$—CH$_3$); 1.34 (3H,t,(—COO—CH$_2$)CH$_3$); 0.95 (6H,m,C$^{18'}$H$_3$+C$^{18}$H$_3$).

EXAMPLE 8

Ethyl N-(O-4deacetyl-vinblastin-23oyl)-L-glutamate (VGE)

Following the general procedure at page 35 VGE was obtained with a 55% yield.

Physico-chemical properties of VGE

Melting point : ~149° C.

[α]D$_{c=2}^{CHCl3}$ : ~59°.

UV spectrum (MeOH, 10 mg/l, λ max, nm, log ε):

IR spectrum (KBr, cm$^{-1}$): 3460; 3395; 2960; 2920; 2870; 1730; 1665; 1610; 1500.

NMR spectrum (CDCl$_3$,ppm,60 HMz): 9.63 (1H, s,C$^{16}$—OH); 8.10 (1H,s,N$^{\alpha'}$—H); 7.6 (1H,m); 7.16 (3H,m); 6.64 (1H,s,C$^9$—H); 6.07 (1H,s,C$^{12}$—H); 5.83 (2H,m,C$^{14}$H+C$^{15}$H); 4.23 (2H,q,—COOCH$_2$—); 4.16 (2H,q,—COOCH$_2$—); 3.8 (3H,s,—OCH$_3$); 3.64 (3H,s,—OCH$_3$); 3.5 (1H,s,C$^5$—H); 2.8 (3H,s,—N$^\alpha$CH$_3$); 1.33 (3H,t,—CH$_3$); 1.26 (3H,t,—CH$_3$); 1 (6H,m,C$^{18}$H$_3$+C$^{18'}$H$_3$).

EXAMPLE 9

Ethyl N-(O-4-deacetyl-vinblastin-23-oyl)-L-phenylalinate (VPE)

Following the general procedure at page 35 VPE was obtained with a 66% yield.

Physico-chemical properties of VPE

Melting point: ~154° C.
$[\alpha]D_{c=1.2}{}^{CHCl_3}$: ~78°.
UV spectrum (MeOH, 9.8 mg/l, λ max, nm, log ε): 219 (4.46); 269 (3.94); 288 (3.80); 296 (3.76).
IR spectrum (KBr, cm$^{-1}$): 3560; 3460; 3400; 2860; 2830; 1730; 1650; 1610; 1500; 1455.
Mass spectrum (m/e %): 958(17); 944(41); 930(35); 871(64); 651(41); 588(41); 571(53); 401(100).
NMR spectrum (CDCl$_3$, ppm, 360 MHz): 9.48 (1H,bs,—C$^{16}$—OH); 8.1 (1H,s,N$^{60}$'—H); 7.6(1H,d); 7.5(1H,d 7.3-7.02 (7H,m); 66 (1H,s,C$^{-9}$—H); 6.1 (1H,s,C$^{12}$—H); 5.87(m,C$^{14}$—H+C$^{15}$—H) (J$^{15-14}$=12 Hz; J$^{14-3}$=8.6 Hz); 4.9

$$\begin{matrix} & O{=}C \\ (1H,m & ; \\ & NHR \end{matrix}$$

4.16 (2H,q,COO—CH$_2$) ; 3.8 (3H,s,—OCH$_3$); 3.43 (1H,s,C$^5$—H); 2.74 (3H,s,N$^\alpha$—CH$_3$); 1.20 (3H,t,—CH$_3$(ester)) 0.97 3H,t,—C$^{18'}$H$_3$; 0.88 (3H,t,—C$^{18}$H$_3$).

EXAMPLE 10

Methyl N-(O-4-deacetyl-vinblastin-23-oyl)-L-isoleucinate (VILM)

Following the general procedure at page 35 VILM was obtained with a 66% yield.

Physico-chemical properties of VILM $[\alpha]D_{c=0\ 135}{}^{CHCl_3}$~66°.
UV spectrum (MeOH, λ max, nm,log ε$_r$): 225 (4.55); 266 (4.18); 288 (4.05); 295 (4.00).
NMR spectrum (CDCl$_3$, 360 MHz): 9.48 (bs,1H,C$^{16}$—OH); 8.03 (s,1H,NH); 7.51 (m,2H); 7.23-7.06 (m,2H); 6.58 (s,1H,C$^9$—H); 6.20 (s,1H,C$^{12}$—H); 5.85 (dd, 1H,C$^{14}$—H ; J$^{15-14}$=12 Hz; J$^{14-3}$=3,6 Hz); 5.78 (d,1H,C$^{15}$—H; 4.62

$$\begin{matrix} & & NH \\ & \diagdown & \diagup \\ (m,1H & C & ); \\ & \diagup & \diagdown \\ & H & COOR \end{matrix}$$

4.17 (d,1H); 3.77 (s,3H,COOCH$_3$); 3.75 (s,3H); 3.6 (s,3H); 2.73 (s,3H,N$^\alpha$—CH$_3$); 2.58 (s,1H,C$^{21}$—H); 0.92 (m,12H,C$^{18}$H$_3$—C$^{18'}$H).

EXAMPLE 11

Ehtyl N-(O-4-deacetyl-vinblastin-23-oyl)-L-tyrosinate (V-Tyr E)

Following the general procedure at page 35 V-Tyr E was obtained with a 48% yield.

Physico-chemical properties of V-Tyr E $[\alpha]D_{C=0.1087}{}^{CHCl_3}$~64°.

UV spectrum (CH$_3$OH, λmax, nm, log ε): 227 (4.73); 266 (4.26); 288 (4.07); 296 (3.94).
IR spectrum (Kbr, cm$^{-1}$): 3460, 3400, 3040, 2950, 2840, 1715, 1660, 1610, 1500, 1455, 1225.
NMR spectrum (360 MHz):
9.6 (bs,1H,C$^{16}$—OH); 8.05 (s,1H,NH); 7.55 (m, 2H); 7.21-7.06 (m,2H); 7.03 (d,2H, arom tyr J=7.5); 6.7 (d,2H,arom tyr.J=7.5); 6.55 (s,1H,C$^9$—H); 6.05 (s,1H,C$^{12}$—H); 5.83 (dd,1H,C$^{14}$—H; J$^{15-14}$=12 Hz; J$^{14-3}$=3.6 Hz); 5.76 (d,1H, C$^{15}$—H); 4.83 (m,1H,CH); 4.13 (massif 3H,—COOCH$_2$, C$^{17}$—H); 3.76 (s,3H); 3.6 (s,3H); 3.45 (s,1H,C$^5$—H); 2.71 (s,3H,—N$^\alpha$—CH$_3$); 1.21 (t,3H,—CH$_3$—(CH$_2$OOC)); 0.88 (m,6H,—C$^{18}$H$_3$—C$^{18'}$H$_3$).

EXAMPLE 12

Ethyl N-(O-4-deacetyl-vinblastin-23-oyl)-L-tyrptophanate (V-Trypt E)

Following the general procedue at page 35 V-Trypt E was obtained with a 72% yield.

Physico-chemical properties of V-Trypt E $[\alpha]D_{c=0.51119}{}^{CHCl_3}$:~90°.
UV spectrum (MeOH, λ max, nm, log ε): 225 (5.15) ; 267 (4.65) ; 280 (ep) ; 290 (4.55).
Mass spectrum (m/e%) Isobutane molecular ionisation: 998 (M$^+$+1+28), 984 (M$^+$+1+14), 970(M$^+$+1), 926; C$_{56}$H$_{68}$N$_6$O$_9$.
IR spectrum (KBr, cm$^{-1}$): 3460, 3400, 3040, 2960, 2940, 2880, 1725, 1660, 1610, 1500, 1455, 1225, 740.
NMR spectrum (CDCl$_3$, 360 MHz): 9.5 (1H,s,C$^{16}$—OH); 8.2 (1H,s,NH,trypt); 8.03 (1H,s,NH); 7.66 (1H,d,trypt; J=7.2 Hz); 7.58 (1H,d,trypt; J=7.2 Hz); 7.51 (1H,d,trypt; J=7.2 Hz); 7.31 (1H,d,trypt; J=7.2 Hz); 7.25-7.04 (5H,m) ; 6.58 (1H,s,C$^9$—H); 6.06 (1H,s,C$^{12}$—H); 5.83 (1H,dd,C$^{14}$—H; J=12 Hz; J=3 6 Hz); 5.78 (1H,d,C$^{15}$—H; J=12 Hz); 4.95 (1H,q,>CH); 3.75 (3H,s,—COOCH$_3$); 3.6 (3H,s,—OCH$_3$); 3.4 (1H,s,C$^5$—H); 2.77 (1H,s,N—CH$_3$); 1.15 (3H,t—COOCH$_2$ (CH$_3$)).

EXAMPLE 13

Methyl N-(O-4-deacetyl-vinblastin-23-oyl)-L-tryptophanate (V-Trypt M)

Following the general procedure at page 35 V-Trypt M was obtained with a 41% yield.

Physico-chemical properties of V-Trypt M $[\alpha]D_{c=1.82}{}^{CHCl_3}$:18 94°.
UV spectrum (MeOH, λ max, nm, log ε): 269 (4.48); 280; 289 (4.32).
IR spectrum (KBr, cm$^{-1}$): 1730, 1710, 1660, 1610, 1495, 1455, 1220, 740.
NMR spectrum (360 MHz): 9.5 (1H,bs,C$^{16}$—OH); 8.06 (1H,s,NH ind); 8.01 (1H,s,NH ind); 7.65 (1H,d); 7.58 (1H,d); 7.38-7.06 (7H,m); 6.41 (1H,s,C$^9$—H); 6.05 (1H,s,C$^{12}$—H); 5.85 (1H,dd,C$^{14}$—H); J=12 Hz; J'=3.6 Hz); 5.78 (1H,d,C$^{15}$—H;J=12 Hz); 4.95 (1H,q,); 4.2 (1H,m,C$^{17}$—H); 3.75 (3H,s,—OCH$_3$); 3.61 (3H,s,—COOCH$_3$); 3.58 (3H,s,—COOCH$_3$); 3.43 (2H,s,C$^5$—H); 2.6 (3H,s,N—CH$_3$).

EXAMPLE 14

Ethyl N-(O-4-deacetyl-vinblastin-23-oyl)-L-valinate (VVE)

Following the general procedure at page 35 VVE was obtained with a 63% yield.

Physco-chemical properties of VVE

UV spectrum (MeOH, λ max, nm, log ε): 226 (4.95); 267 (4.57); 285 (4.45); 296 (4.40).

Mass spectrum (m/e%): 910 (0,1); 896 (2); 882(5); 823(4.5); 822(6); 708(5.3); 653(9.2); 651(8.7); 650(14.6); 572(8.7); 571(23.3); 539 (10.7); 355(16); 354(10); 353(31); 294(17); 188(8.5); 156(100); 155(11.8); 154(11.3); 144(12.2); 141(12.1); 140(16.4); 136(13); 135(20.4); 124(61); 122(35.5); 121(15.3).

IR spectrum (KBr, cm$^{-1}$): 3540, 3470, 3420, 2960, 2930, 2870, 1730, 1720, 1670, 1610, 1500, 1455, 1225, 745.

NMR spectrum: 9.48(1H,bs,$C^{16}$—OH); 8.03 (1H,bs,NH ind); 7.55 (1H,d;J=7.2 Hz); 7.51 (1H,d,J=7.2 Hz); 7.51 (1H,d); 7.23–7.06 (3H,m); 6.58 (1H,s,$C^9$—H); 6.06 (1H,s,$C^{12}$—H); 5.85 (1H,dd,$C^{14}$—H; $J^{14-15}$=12 Hz; $J^{14-3}$=3.6 Hz); 5.78 (1H,d,$C^{15}$—H; J=12 Hz); 4.56 (1H,dd,C); 4.21 (2H,q,COOCH$_2$); 4.15 (1H,d,$C^{17}$—H); 3.96 (1H,t); 3.76 (3H,s,OCH$_3$); 3.6 (3H,s, COOCH$_3$); 3.46 (1H,s,$C^5$—H); 2.73 (3Hs,N—CH$_3$); 1.31 (6H,m,COOCH$_2$CH$_3$); 0.96 (14H,m); 0.9 (14H,t).

EXAMPLE 15

Ethyl N-(O-4-deacetyl-vinblastin-23-oyl)-L-iso-leucinate (VILE)

Following the general procedure at page 35 VILE was been obtained with a 58% yield.

Physico-chemical properties of VILE

UV spectrum (MeOH, λ max, nm, log ε): 226 (4.94); 266 (4.56); 285 (4.44); 295 (4.38).

Mass spectrum (m/e %): 924 (7); 910(11); 897(23); 896(44.4); 867(11,3); 837(18.7); 836(26.6); 822(4); 709(10); 650(21); 571(13); 570(34.7); 366(21.7); 154(100); 126(11).

IR spectrum (KBr, cm$^{-1}$): 3460, 3440, 3040, 2960, 2940, 2880, 1730, 1665, 1610, 1500, 1455, 1225, 745.

NMR spectrum (CDCl$_3$, 360 MHz): 9.46(1H,bs,$C^{16}$—OH); 8.03(1H,bs,NH); 7.55(1H,d;J=7.2 Hz); 7,51(1H,d); 7.23–7.06 (3H,m); 6.58 (1H,s,$C^9$ —H); 6.06 (1H,s,$C^{12}$ —H); 5.85 (1H,dd,$C^{14}$—H; J=12 Hz; J'=3,6 Hz); 5.78 (1H,d,$C^{15}$—H); J=12 Hz); 4.61 (1H,q(dd), C); 4.21 (2H,q,COO—CH$_2$—); 4.15 (1H,d,$C^{17}$—H); 3.96 (1H,t); 3.76 (3H,s,OCH$_3$ ester 3.6 (3H,s,OCH$_3$); 3.46 (1H,s,$C^5$ —H); 2.73(3H,s,N—CH$_3$); 1.25 (3H,t,COOCH$_2$CH$_3$).

EXAMPLE 16

Ethyl N-(O-4-deacetyl-vinblastin-23-oyl)-D-tryptophanate (VD Trypt E)

Following the general procedure at page 35 VD Trypt E was obtained with a 69% yield.

Physico-chemical properties of VD Trypt E $[\alpha]_{Dc=0.3295}^{CDCl_3}$: 70°.

UV spectrum (MeOH, λ max, nm, log ε): 225 (4.77); 269 (4.30); 290 (4.20); 320 (ep).

Mass spectrum (m/e %): 970, 391, 279, 165, 108, 35.

IR spectrum (KBr, cm$^{-1}$): 3460, 3400, 3050, 2960, 2940, 2870, 1735, 1665, 1610, 1495, 1455, 1210, 740.

NMR spectrum: 9.53 (1H,bs,$C^{16}$ —OH); 8.1 (1H,s,NH ind tryp); 8.02 (1H,s,NH ind); 7.76 (1H,d); 7.65 (1H,d); 7.51 (1H,d); 7.35 (1H,d); 7.2–7.05 (6H,m); 6.53 (1H,s,$C^9$H); 5.98 (1H,dd,$C^{14}$H $J^{14-15}$=12 Hz,$J'^{14-3}$=3.6 Hz); 5.73 (1H,d,$C^{15}$—H; J=12 Hz); 4.86 (1H,q,C—); 4.1 (3H,m,$C^{17}$—H—COOCH$_2$); 3.75 (3H,s,COOCH$_3$); 3.6 (3H,s,—OCH$_3$); 3.33 (2H,s,$C^5$—H); 2.43 (3H,s,N—CH$_3$); 1.16 (3H,t,—COOCH$_2$—CH$_3$); 0.93 (8H,m).

EXAMPLE 17

Ethyl N-(O-4-deacetyl-vinblastin-23-oyl)-L-valyl-L-tryptophanate (V-Val-Trypt-E)

Following the general procedure at page 35 V-Val-Trypt E was obtained with a 40% yield.

Physico- chemical properties of V-Val-Trypt-E $[\alpha]_{Dc=0.3589}^{CHCl_3}$: 36°.

UV spectrum (methanol, λ max, nm, log ε): 270 (4.42); 290; 312 (4.96).

IR spectrum (KBr, cm$^{-1}$): 3480, 3400, 2960, 2940, 2870, 1735, 1725, 1660, 1610, 1500, 1455, 1230.

NMR spectrum (CDCl$_3$, 360 MHz): 9.5 (1H,bs,$C^{16}$—OH); 8.18(1H,s,NH ind); 8.01 (1H,s,NH ind); 7.6–7.06 (10 H,m,arom); 6.41 (1H,s,$C^9$ —H); 5.95(1H,s,$C^{12}$ —H); 5.85 (1H,dd,$C^{14}$ —H; $J^{15-14}$=12 Hz; $J^{8-14}$=3,6 Hz); 5.75 (1H,d,$c^1_*$—H; $J^{15-14}$=12 Hz); 5.02 (1H,m,C); 4.9 (1H,m,C); 3,73 (3H,s,COOCH$_3$); 3.56 (3H,s,—OCH$_3$); 3.43 (2H,s,$C^5$ —H); 2.61 (3H,s,N—CH 1.05–0.86 (±16H,m,CH$_3$).

EXAMPLE 18

Ethyl N-(O-4-deacetyl-vinblastin-23-oyl)-L-leucyl-L-alanyl L-leucyl-L-alanylate (V-Leu-Ala-Leu-Ala-E)

In accordance with the general procedure and preparing the azide from 700 mg monohydrazide, the reaction with 377 mg ethyl-L-Leu-L-Ala-L-Leu-L-Alaninate at 4° C. for 60 h yielded 213 mg pure V-Leu-Ala-Leu-Ala-E. The purification was effected by passing the crude product first on a column of silica 60 Merck (230 mesh) using as eluant a mixture ether-MeOH sat NH$_3$ (86:14), then on an identical column using as eluant a mixture of isopropanol-ethyl-acetate-cyclohexane (40:20:40).

Physico-chemical properties of V-Leu-Ala-Leu-Ala-E

UV spectrum (methanol, 5.74 mg/100 cc, log ε): 266 (4.24); 2.85–288 (4.12); 296 (4.07).

Mass spectrum (isobutane DCI, molecular ionisation): 1152 (M$^+$+1), 1166 (M$^+$+1+14), 1134, 1108, 1094.

IR spectrum (KBr): 3400, 2960, 1740, 1660, 1620, 1506, 1460, 1225, 745 cm$^{-1}$.

NMR spectrum (CDCl$_3$, 360 MHz, ppm): 0.91, 1.27 (t), 1.40 (2d), 1.67 (d×d), 2.61 (s), 2.72 (s) 3.60 (s), 3.75 (s), 4.19 (q), 5.74 (d), 5.83 (d×d), 6.03 (s) 6.59 (s), 6.88 (d), 7.00 (d), 7.39 (d), 7.49 (d), 7.53 (d) 8.02 (s), 9.57 (s).

EXAMPLE 19

Ethyl N-(O-4-deacetyl-vinblastin-23-oyl-L-tryptophyl-L-tryptophanate (V-Tryp-Tryp-E)

In accordance with the general procedure and using 1 g hydrazide and 543 mg ethyl L-tryptophyl-L-triptophanate, 268 g of pure V-Tryp-Tryp-E have been produced by passing the crude product on a column of silica using as eluant first a mixture ether-methanol sat. $NH_3$ (92:8) then an identical mixture but 86: 14.

Physico-chemical properties of V-Tryp-Tryp-E

UV spectrum (MeOH) (49,6 mgl ): max 272 (4.38); 278 (4.37); 290 (4.31); min 248 (4.18), 288 (4.30).

Mass spectrum (DCI isobutane): 1184; 1170; 1156 ($M^+ + 1$); 1112; 1098; 624; 498; 165.

IR spectrum (Kbr): 3410; 2970; 2880; 1725; 1665; 1615; 1500; 1460; 1230 $cm^{-1}$.

EXAMPLE 20

Ethyl N-(O-4-deacetyl-vinblastin-23-oyl)-L-tryptophylglycinate (V-Tryp-Gly-E)

Condensation of 596 mg hydrazide and 226 mg ethyl L-tryptophylglycinate (41h, 4° C.) give 200 mg V-Tryp-Gly-E after purification on a silica column using as eluant a mixture ether-methanol wherein the proportion of $CH_3OH—NH_3$ is increased from 4 to 14%.

Mass spectrum (molecular ionisation with isobutane): $M^+ + 1$ 1027, 1042, 1055, 1013, 983, 969.

EXAMPLE 21

Ethyl N-(O-4-deacetyl-vinblastin-23-oyl)-L-valinyl-L-tryptophanate (V-Val-Tryp-E)

From 500 mg hydrazide of deacetyl-VLB and 215 mg ethyl L-valinyl-L-tryptophanate, 215 mg pure V-Val-Tryp-E have been obtained after column chromatography.

Mass spectrum (molecular ionisation $NH_3$): $M^+ + 1$ 1069, 632, 617, 498, 332, 223.

EXAMPLE 22

Ethyl N-(vinblastin-23-oyl)-L-valinate

Ethyl N-(O-4 deacetyl vinblastin-23-oyl-L-valinate (100 mg) was reacted with a mixture of pyridine (2.5 mL), acetic anhydride (2.5 mL) under inert atmosphere and stirring for 24 h. After adding methanol and concentration under reduced pressure, the product was dissolved in dichloromethane and washed with NaCl sat. water. The organic phase was dried on $Na_2SO_4$ and concentrated under reduced pressure. The product is purified by t.l.c. using as eluant a mixture isopropanol-/ethylacetate/cyclohexane (40/20/40). 29 mg of ethyl N-(vinblastin-23-oyl)-L-valinate was thus obtained.

Mass spectrum (molecular ionisation isobutane): $M^+ + 1$ 925; $M^+ + 1 + 14$ 939; $M^+ + 1 + 28$ 953; 924; 907; 893; 882; 881; 867; 866; 392; 279.

IR spectrum (Kbr, $cm^{-1}$): 3480, 3430, 2970, 1740, 1690, 1615.

UV spectrum (54,2 mg/L, λ max, log ε): 263 (4.28); 288 (4.17); 296 (4.13).

EXAMPLE 23

Ethyl N-(-O-4-deacetyl-4'-deoxy-vinblastin-23-oyl-B)-isoleucinate

A solution of O-4-deacetyl-4'-deoxyvinblastine B hydrazide (0.6 g, 0.79 mM) in a mixture of 15 ml $CH_3OH$ and 45 ml HCl 1N was cooled to $-7°$ C. (see U.S. Pat. No. 4,203,898 column 24, line 51 et seq.). $NaNO_2$ was added to the solution (0.15 g) and stirring was continued for 13 minutes at $-7°$ C. After addition of an aqueous saturated solution of $NaCH_3$ till a pH of 9 is obtained, the resulting solution was extracted four times with $CH_2Cl_2$. The combined organic phases were washed with sat. aqueous NaCl solution and dried over $MgSO_4$.

The solution was concentrated to a volume of 15 ml and ethyl isoleucinate (1.25 mM) was added. The reaction mixture was allowed to stand 4 days in a refrigerator. The solvent was then evaporated under reduced pressure. The residue was purified by column chromatography ($SiO_2$, 60 g) and eluted with ether: $CH_3OH/NH_3$ (96:4) to afford 0.25 g of amorphous product (yield 35%).

Physico-chemical properties of deoxy VILE

Mass spectrum (Molec. Ionisation isobutane): 880 ($M^{+^\circ}$, 894, 836, 849, 823, 445, 391, 355 $cm^{-1}$; $C_{51}H_{69}N_5O_8 = 880.1$.

Melting point 180°–190° C.

$a_D = 104°$ (c=0.154).

IR (CHCl3): 3470, 2970, 1728, 1655, 1612, 1502 $cm^{-1}$.

UV (CH3OH): 289, 268, 216 nm.

NMR (CDCl3): 7.9 (NH), 654 and 6.06 H9,H12 5.81 (H14-H15) 4.60 (CHCO2(NH)) 3.76 $CO_2CH_3$, 3.58 $CH_3—O$, 3.33 and 2.85 (H3A and H3B), 2.73 (N—CH3), 0.69 (H-15').

EXAMPLE 24

Ethyl N-(O-4-deacetyl-4'-deoxyvinblastin-23-oyl-B)-tryptophanate

O-4-deacetyl-4'-deoxyvinblastine B carboxhydrazide (1.25 g, 1.66 mM) was dissolved in 30 ml of methanol and 100 ml HCL 1N. The mixture was cooled at $-50°$ C.

There was added $NaNO_2$ (0.240 g) and the reaction mixture was stirred at $-10°$ C. for 10 minutes. After addition of an aqueous sat. solution of $NaHCO_3$ till a pH of 9 was obtained, the resulting mixture was extracted 4 times with $CH_2Cl_2$.

The combined organic phase was washed with aqueous sat. NaCl solution and dried over $MgSO_4$.

The solution was concentrated until about 20 ml remained and Ethyl L-tryptophanate was then added (0.45 g, 1.93 mM).

The reaction mixture was allowed to stand for 3 days in a refrigerator. The reaction being then complete, the solvent is vacuum evaporated. The resulting residue was purified by column chromotography ($SiO_2$, 70 g) using an eluent ether-methanol saturated with $NH_3$, the proportion of the latter solvents changing gradually from 96:4 to 84:16 (v:v).

There was obtained 0.60 g of O-4-deacetyl-4'-deoxy VLB Trypt E which was easily recristallised in ethanol. Overall yield 38%.

NMR spectrum (360 MHz, CDCl₃, ppm): 0.70, 2.00 (H15,H15'), 0.86 (CH₃-18', 0.96 CH₃-18) 1.15 (CH₃—CH₂O), 2.74 (CH₃—N) CH₃—O—Ph 3.56, 3.75 (CO₂CH₃), 4.02 (CH₂—O—), 4.16 (H17) 4.90 (CH NH CO), 5.78, 6.01 and 6.51 (H9-H12).

Mass spectrum (molecular ionisation isobutane): 981, 968 954 (M⁺), 938, 924, 910, 500, 469, 393 calculated for C₅₆H₆₈N₆O₈ 953.194.

α_D 133° c=0.17.

Melting point 210°–220° C.

UV (CH₃OH), nm): 290, 272.

IR spectrum (4%, CHCl₃): 3487, 3400, 3000, 2963, 2920, 1727, 1663, 1614, 1410 cm⁻¹.

EXAMPLE 25

1. O-4-deacetyl N-desformyl vincristine monhydrazide

Vincristine base (985 mg) was dissolved in a mixture of 10 ml anhydrous hydrazine and 10 ml of methanol. The reaction mixture was heated at 60° C. under stirring for 22 hours. The resulting solution was then successively treated with water and NaCl saturated aqueous solution.

The non-organic phase was extracted 8 times with 15 ml of dichloromethane. The combined organic phases were washed again with water and NaCl saturated water, then dried over Na₂SO₄. After filtration and concentration under vacuum O-4 deacetyl N-desformyl vincristine monohydrazide was then collected (900 mg, purity over 90%).

NMR spectrum (CDCl₃ 360 MHz): 9,76 (s,1H) 8.37 (s,1H), 8,06 (s, 1H), 7,53 (d, 1H) 7,24 and 7,07 (m,3H), 6,82 (s,1H), 6,22 (s,1), 5,87 (dd,1h), 5,67 (d,1H), 5,43 (s, 1H), 4,03 (s,1H), 3,94 (s, 3H), 3,86 (s, 1H) 3,73 (s, 3H), 3,52 (s, 3H) 2,82 (s, 2H), 2,51 (s, 1H) 0,93 (2t, 2×3H).

Mass spectrum (Mol. Ionis.): 154, 294, 355, 413, 524, 555, 695, 10, 723, 736, 739, 755 (M+1)—768, 769, 782 calculated for C₄₂H₅₄N₆O₇ 754.942.

2. O-4-deacetyl-N-desmethyl VLB carboxazide

A solution of O-4-deacetyl-N-desmethyl VLB carboxhydrazide (850 mg) in 20 ml of methanol was treated with HCl 1N (63 ml) and sodium nitrite (175.5 mg) for 15 minutes at 0° C. The solution was maintained at 0° C. and neutralised with NaHCO₃, then extracted six times with 15 ml of dichloromethane. The combined organic phases were dried over Na₂SO₄, filtrated and vacuum concentrated without heating until a solution of about 10 ml remained.

3. Ethyl N-(O-4-deacetylvincristin-23-oyl)-tryptophanate

Ethyl tryptophanate (300 mg) was added under stirring at 4° C. The reaction mixture was monitored by thin layer chromatography (tlc). After 10 days at 4° C., the coupled product was purified using chromatographic separation (silicagel, 40 g, elution with ether, methanol (v:v, 96:4) sat. with NH₃). There was collected 15 ml fractions which were analysed by tlc. Free ester of amino acid was first detected (fraction 30 to 40). Elution solvent was then changed to ether, methanol 86:14 sat. with NH₃ and there was further collected 3 groups of fractions:

fractions 44–45: 30 mg
fractions 46–53: 257 mg
fractions 54–60: 115 mg

The second group of fractions contained pure (by tlc) ethyl N-(O-4-deacetyl desformyl vincristin-23-oyl) tryptophanate.

Mass spectrum (molecular ionisation isobutane): 984, 970, 956 (M⁺+1) 913, 912, 899 calculated for C₅₅H₅₆N₆O₉: 955.

UV Spectrum (CH₃OH, log ε, nm): λmax: 282 (4.20)–290 (4.18)–(3.96); λmin: 254–287–305.

IR Spectrum: (cm⁻¹) 3400–2920–1720–1660–1610–1485–1450–1370; 1345–1330–1290–1220–1165–1130–1025–1005; 920–885–830–740.

NMR Spectrum (CDCl₃) 360 MHZ (ppm): 8.50 (s, 1H); 8.03 (s, 2H); 7.77 (d, 1H); 7.60 (d, 1H); 7.57 (d, 1H); 6.95 (s, 1H); 6.35 (s, 1H); 5.89 (d.d., 1H); 5.78 (d, 1H); 4.75 (q, 1H); 3.88 (s, 3H); 3.67 (s, 3H); 1.23 (t, 3H); 0.98 (t, 3H); 0.89 (t, 3H).

EXAMPLE 26

Ethyl N-(O-4-deacetyl vincristin-23-oyl)-tryptophanate

Deformylated compound of the preceeding example (257 mg) was reformylated using the method and conditions described in Belgian Patent No. 811,110. The resulting crude product was purified by column chromatography (silica gel, 30 g, 20 cm) using successively 3 eluents, ether-methanol sat. with NH₃ (92:8; 88:12; 86:14). The eluate was collected in 15 ml fractions. Fractions 44 to 54 (34.1 mg) contained a compound whose physico-chemical properties were in accordance with the desired N-reformylated derivative.

Mass spectrum (molecular ionisation isobutane): 1011, 997, 983 (M+1), 970, 982, 996, 998, 999, calculated for C₅₆H₆₆N₆O₁₀=983,192.

UV spectrum (CH₃OH, log ε, nm): λmax: 270 (4.18)–290 (4.11).

IR spectrum (KBr, cm⁻¹): 3400–3040–2960–2920–2880–2850–1735–1725–1680–1670–1665–1610–1490–1450–1225–745.

EXAMPLE 27

1. 10'-bromovinblastine

To a solution of vinblastine sulphate (2 g, 2.2 mM) in 200 ml of trifluoroacetic acid, there was added dropwise under argon and at room temperature, a solution of N-bromosuccimide (408 mg, 2.3 mM) in 100 ml trifluoroacetic acid.

The reaction mixture was further stirred for 64 hours in the absence of light. After having checked the disappearance of vinblastine (tlc silica gel, ethanol-ethyl acetate, 1:1), 200 ml of trifluoroacetic acid were removed under vacuum and the residual solution was poured onto crushed ice. The mixture was thereafter made basic with diluted ammonia (t=20° C.) and the aqueous solution was extracted several times with dichloromethane. The combined organic phases were washed with water, dried over MgSO₄ and vacuum extracted to dryness. The residue (1.9 g) was placed over a silica gel (57 g) column prepared with ethyl acetate-ethanol (95:5). The mixture was eluated with successive portions of ethyl acetate-ethanol of increasing polarity. The combined fractions collected with ratio of eluents 92.5:7.5 were identical by tlc analysis. Classical work-up of this solution afforded 0.93 g (yield 47.5%) of amorphous 10'-bromo-vinblastine.

Mass spectrum (molecular ionisation isobutane, m/e): M⁺+1=890 (Br⁷⁹, 7.59%); M⁺+1=892 (Br⁸¹, 5.52%). 73 (85%), 74 (100%), 83 (48%), 108 (92%), 122

(58%) 214 (49%) - 223 (60%) - 279 (71%) - 391 (25%) - 435 (6%) - 889 (5.5%) 891 (3.29%) - 893 (4.1%)

IR spectrum (KBr, cm$^{-1}$): 3460–2960–1880–2840–2800–1740–1615–1502–1470–1430–1370–1310–1250–1230–1040–1010–935–900–800–760.

UV spectrum (CH$_3$OH, nm, log ε): max: 216 (4.67)–298 (4.07); min: 280 (3.97)

NMR spectrum (CDCl$_3$, ppm, 360 MHz): s, broad, 9.82 (OH); s., 8.08 (NH); d.,J=2 Hz; 7.62 (H$_{9'}$); d.d., J=9 Hz, J'=2 Hz, 7.22, (H$_{11}$,); d., J=9 Hz, 6.97, H$_{(12)}$; s., 6.52 (H$_9$); s., 6.10 (H$_{12}$); d.d, J=10 Hz, J=4 Hz, 5.87 (H$_{14}$); s., 5.47 (H$_{17}$)d., J=10 Hz, 5.28; (H$_{15}$); s. 3.80, (2 CO$_2$CH$_3$); s., 3.7 (H$_{21}$); s., 3.63, (Ar—OCH$_3$); s., 2.72, (N—CH$_3$); s., 2.12 (OCOCH$_3$); t.,J=7 Hz, 0.89 (—CH$_2$—CH$_3$); t., J=7 Hz, 0.78 (—CH$_2$—CH$_3$).

2. 10'-bromovinblastine sulphate

To a solution of 10' bromovinblastine as a base (1.89 g) in 20 ml of pure ethanol, there was added dropwise under stirring a 1% ethanolic solution of sulfuric acid.

The dropwise addition was stopped at pH 4.

The stirring was maintained for ½ hour at room temperature and the solution was allowed to stand for a night in a refrigerator. The resulting white crystals were filtrated, washed with ethanol then with ether and dried under vacuum. There was obtained 1.40 g of 10'-bromovinblastine sulphate (yield=66.7%).

Melting point: ~255° C.

Optical rotation, α$_D$≈−34.7° (H$_2$O, c=0.26).

EXAMPLE 28

10'-bromo-O-4-deacetyl vinblastine (a) 310 g of 10'-bromovinblastine was solubilised in 50 ml of methanol. The solution was cooled under 0° C. and saturated with gaseous HCl by bubbling, care being taken to keep the temperature below 0° C. After stirring at room temperature for 48 hours, tlc indicated the presence of a more polar derivative. The mixture is poured onto 200 g of crushed ice and alkalinized with concentrated ammonia. After extraction with CH$_2$Cl$_2$, the organic phase was washed with water and dried over MgSO$_4$. The solvent was distilled off at reduced pressure. There was obtained a product homogeneous by tlc and identifed as the 04-deacetyl derivative of the starting product (250 mg, yield=84.6%). The residue may optionally be purified by thin layer preparative chromatography (silica gel G 60) using as eluants a mixture ether-methanol saturated with ammonia 85:15).

α$_D$= ~19.5°(c=0.1; CHCl$_3$).

(b) To a solution of O-4 deacetylvinblastine (157 mg) in 16 ml of trifluoroacetic acid, there was added 16.4 ml of a brominating solution prepared from 113.3 mg of N-bromosuccinimide which has been solubilised in 50 ml of trifuloroacetic acid. The reaction mixture was stirred at room temperature for 64 hours with exclusion of light. After checking by tlc the completeness of the reaction, the mixture was diluated with 300 ml of CH$_2$Cl$_2$ and the resulting solution is poured onto 400 g of crushed ice. With good stirring, the pH was brought to 9 by addition of 14N aqueous ammonia.

After decantation, the water phase was extracted twice with dichloromethane. The combined extracts were washed with water, dried over MgSO$_4$ and the solvent was distilled off to dryness. The residue (173 mg) was placed on two silica gel plates (20×20 cm of 0.7 cm of thickness. Chromatography was performed eluting with ether-methanol (85-15) saturated with NH$_3$. Classical work-up afforded 79 mg (yield 45%) of 10'-bromo-04-deacetylvinblastine identical with a sample obtained by the method described in (a).

(c) 0.91 ml of a brominating solution, prepared by dissolving 281 mg of Br$_2$ in 100 ml of CHCl$_3$, was added to a solution of deacetylvinblastine (12.3 mg) in 6 ml of CHCl$_3$. After stirring at room temperature for 24 hours, the reaction mixture was analysed by tlc which confirmed the reaction was complete. The mixture was made alkaline by adding and stirring with aqueous ammonia 3.5 N. Work-up as described in (b) afforded 6 mg of bromo-10'-bromo-04-deacetylvinblastine identical with samples obtained in (a) or (b).

EXAMPLE 29

10'-bromovincristine

A brominating solution was prepared by dissolving 142 mg of N-bromosuccinimide in 50 ml of trilfuoroacetic acid. 39.8 ml of such solution was added to vincristine sulphate (534 mg, 0.58 mM) dissolved in 22 ml of trifluoroacetic acid. After 4 hours, tlc analysis indicated that the reactio was nearly complete.

There was added additional 3 ml of brominating solution. Tlc analysis after 15 minutes indicated disappearance of the starting vincristine. The mixture was treated as in example 27. There was obtained 506.6 mg of crude brominated product which was purified by column chromatography (silica 60).

optical rotation: α$_D$≈+20° (CHCl$_3$, c=0.28).

UV spectrum (CH$_3$OH, log ε, nm): λ max 225 (4.66)–306 (4.26); λ min 276 (3.97); λ sh: 255 (4.33)–264 (4.21).

EXAMPLE 30

10'-bromo-O4-deacetyl-3-deacarbomethoxy-vinblastine-3-carboxhydrazide

10'-bromovinblastine (450 mg) was dissolved in 4.5 ml of a 50:50 mixture of an hydrous hydrazine and methanol. The resulting mixture was heated under argon at 60° C. for 22 hours. The reaction was monitored by tlc analysis (silica 60 plates - eluents ether-methanol (86:14) saturated with ammonia. The reaction mixture was then treated with NaCl sat. water and extracted 8 times by 15 ml of dichloromethane. The combined extracts were washed with 20 mg of water and 25 ml of NaCl sat. water, then dried over Na$_2$SO$_4$.

After distilling off the solvent, there was provided 405 mg of 10'-bromo-04-deacetylvinblastine monohydrazide (yield 94%).

UV spectrum (CH$_3$OH, logε, nm) λ max: 299 (4.07); λ min: 284 (4.02); λ sh: 267 (4.24)–302 (4.06).

IR spectrum KBr, cm$^{-1}$: 3440–2960–2930–2880–1720–1660–1615–1500.

NMR spectrum (CDCl$_3$, 360 MHz): H$_{17}$ (d), 4.15 ppm; C$_{16}$—CO$_2$CH$_3$ (s) 3.77 ppm —OCH$_3$ (s,3H) 3.62.

EXAMPLE 31

Ethyl N-(10'bromo-04-deacetyl-vinblastin-23-oyl)-L-tryptophanate

10'-bromo-04-deacetyl-vinblastine monhydrazide (383 mg, 4.52 10å)M was dissolved in 8.8 ml of methanol and 28.3 ml of HCl 1N. The solution was cooled to 0° C. Sodium nitrite (79.1 mg) was then added to the solution and stirring was continued for 15 minutes at 0° C. The pH was adjusted to 8.5 by addition of an aqueous 5% NaHCO$_3$ solution. The azide which was produced was extracted with 6 portions of 15 ml of CH$_2$Cl$_2$. The combined extracts were dried over Na₂SO₄ and concentrated until a volume of 10 ml was reached. There was then added to this azide solution 120 mg of ethyl L-tryptophanate as a base and the mixture was allowed to stand in a refrigerator for 7 days.

The solvent is afterwards evaporated off and the residue was purified by column chromatography (25 g of silica 60) and eluated by portions of 10 ml successively with mixture of ether-methanol saturated with NH₃ in the proportions 96:4 (31 fractions), 86:14 (fractions Nos. 32–50). Fractions 33 to 42, homogeneous by tlc analysis, were combined and concentrated to afford 236 mg of the title compound.

The corresponding sulphate was obtained by adding 812 ml of 2% H₂SO₄-ethanol (0.393 mEq) of sulfuric acid to a solution of 206 mg of the bromo derivative (0.197 mEq).

Mass spectrum (molecular ionisation NH₃): 1047 (8.2%), 1049 (11.5%), 408–392 (23%), calculated for C₅₆H₆₇N₆O₉Br=1048.1.

UV spectra (CH₃OH, log ε, nm): λ max 263 54.34–290 (4.20); λ min 254 (4.33), 287(4.18); λ sh 308.

optical rotation, $a_D = +79°$ (CHCl₃, c=0.1).

We claim:

1. A vinblastine group of the formula

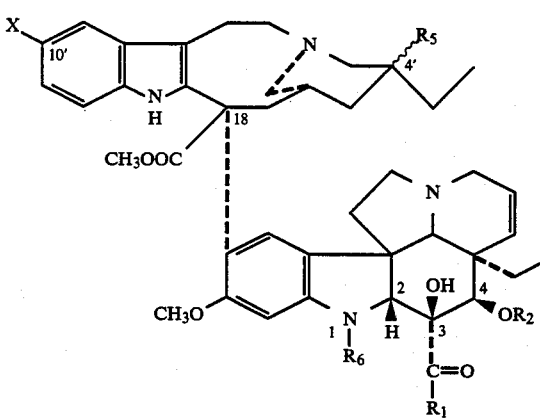

(I)

wherein R₁ is an ester, attached through the nitrogen of a α-aminoacid selected from the group consisting of glycine, alanine, valine, leucine, isoleucine, serine, threoinine, aspartic acid, glutamic acid, aspargine, glutamine, arginine, lysine, cysteine, cystine, methionine, phenylalanine, tyrosine, tryptophan, proline, histidine, hydroxy-lysine, hydroxyproline, or of a peptide consisting of 2–6 identical or different such amino-acids, and the ester group, which may be straight or branched, being a carboalkoxy group having 2–9 carbon atoms, and R₂ is hydrogen or a C₂–C₉ alkanoyl group, R₅ is H or OH, R₆ is CH₃, CHO or H and X is Br and their pharmaceutically acceptable mineral or organic acid addition salts.

2. A vinblastine group of the formula

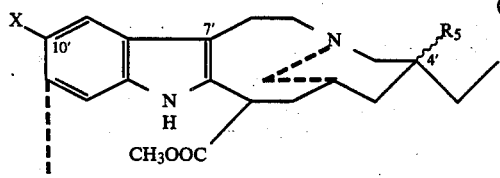

(II)

-continued

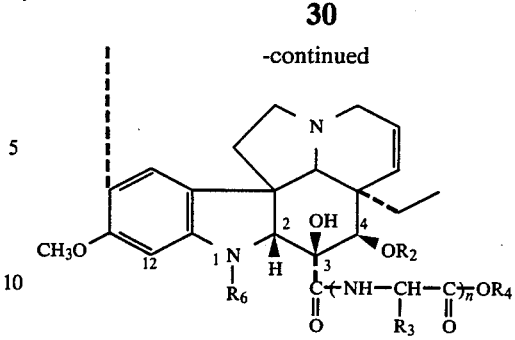

wherein R₂ is a hydrogen atom or a C₂–C₃ alkanoyl group, R₃ is a hydrogen atom, straight or branched C₁–C₈ alkyl, hydroxy - C₁–C₈ -alkyl, carboxy -C₁–C₈ -alkyl, amido -C₁–C₈- alkyl, amino -C₁–C₈-alkyl or hydroxyalkyl, guanadino -C₁–C₈- alkyl, sulfydryl -C₁–C₈alkyl, methylthio-ethyl, benzyl, hydroxy-benzyl, or a group:

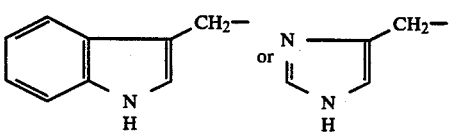

or R₃ together with the carbon to which it is attached and the amido nitrogen, forms an azole or an hydroxyazole ring; n is an integer of from 1 to 6; and R₄ is a straight or branched C₁–C₈-alkyl, or a benzyl group R₅ is H or OH; R₆ is CH₃, CHO or H and X=Br, and their pharmaceutically acceptable mineral and organic acid addition salts.

3. A compound of the formula

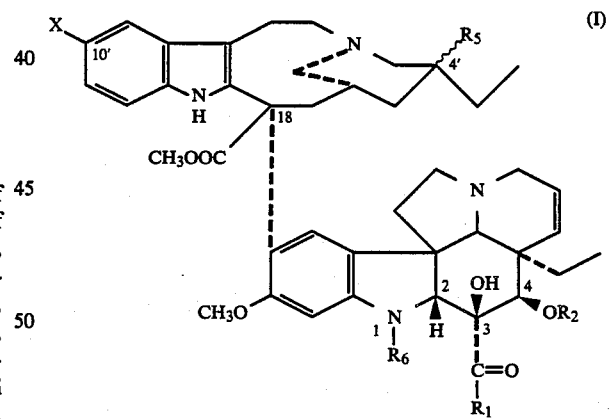

(I)

wherein R₁ is an ester, attached through the nitrogen, of L-tryptophan and the ester group, which may be straight or branched, is a carboalkoxy group, R₂ is hydrogen or a C₂–C₉ alkanoyl group, R₅ is H or OH, R₆ is CH₃, CHO or H, and X is H or Br, and its pharmaceutically acceptable mineral or organic acid addition salts.

4. A compound in accordance with claim 2, wherein the addition salt is the 1:1 addition salt with sulfuric acid.

5. The sulfuric acid addition salt of a compound selected from the group consisting of:
    ethyl N-(O-4-deacetyl-4'-deoxy-vinblasti-23-oyl-B)-L-tryptophanate ethyl N-(10'-bromo-O-4-deacetylvinblastin-23-oyl-B)-L-tryptophanate wherein said addition salt is in a ratio of 1:1.

6. Ethyl N-(O-4-deacetyl-4'-deoxy-vinblastin-23-oyl-B)L-tryptophanate sulphate or methane sulfonate.

7. A compound in accordance with claim 1 which is Ethyl N-(10'-bromo-O-4-deacetylvinblastin-23-oyl)L-tryptophanate and its pharmaceutically acceptable mineral or organic acid addition salts.

8. A vinblastine derivative according to claim 1 in which $R_5$ is hydrogen.

9. A vinblastine derivative according to claim 1 in which $R_6$ is CHO or hydrogen.

10. A vinblastine derivative according to claim 2 in which $R_5$ is hydrogen.

11. A vinblastine derivative according to claim 2 in which $R_6$ is CHO or hydrogen.

12. A derivative of vinblastine selected from the group consisting of
   10'-bromovinblastine,
   10'-bromo-O-4-deacetylvinblastine,
   10'-bromo-vincristine,
   10'-bromo-O-4-deacetyl-3-decarbomethoxyvinblastine-3-carboxhydrazide,
and their pharmaceutically acceptable mineral or organic acid addition salts.

13. Pharmaceutical composition for use in human or veterinary medicine for treating leukemia, solid tumors treatable with vinblastine, vincristine or vindesine or Hodgkins disease containing a compound in accordance with claim 12 in an amount of about 2–900 mg in a unitary dose.

14. Pharmaceutical composition for use in human or veterinary medicine for treating leukemia, solid tumors treatable with vinblastine, vincristine or vindesine or Hodgkins disease containing a compound in accordance with claim 2 in an amount of about 2–900 mg in a unitary dose.

15. Pharmaceutical composition in accordance with claim 14 wherein the active compound is ethyl N(O-4-deacetyl-4'-deoxy-vinblastin-23-oyl-B)-L-tryptophanate and its addition salt with a pharmaceutically acceptable salt.

16. Pharmaceutical composition in accordance with claim 14 wherein the active compound is in a pharmaceutically acceptable diluent.

17. Pharmaceutical composition in accordance with claim 16 wherein the diluent is a sterile buffered aqueous solution.

18. Pharmaceutical composition for use in human or veterinary medicine for treating leukemia, solid tumors treatable with vinblastine, vincristine or vindesine or Hodgkins disease containing a compound in accordance with claim 3 in an amount of about 2–900 mg in a unitary dose.

19. The method of treating leukemia, solid tumors treatable with vinblastine, vincristine or vindesine or Hodgkins disease which comprises administering to a cancer patient in therapeutically effective amount, a compound as defined in claim 2.

20. The method of treating leukemia, solid tumors treatable with vinblastine, vincristine or vindesine or Hodgkins disease which comprises administering to a cancer patient in therapeutically effective amount, a compound as defined in claim 3.

* * * * *